US010214561B2

(12) United States Patent
Shimizu et al.

(10) Patent No.: US 10,214,561 B2
(45) Date of Patent: Feb. 26, 2019

(54) PEPTIDE HAVING ACTIVITY OF INHIBITING PRODUCTION OF TOXIN BY BACTERIUM BELONGING TO GENUS CLOSTRIDIUM

(71) Applicant: MIYARISAN PHARMACEUTICAL CO., LTD., Nagano (JP)

(72) Inventors: Tohru Shimizu, Nagano (JP); Kaori Ohtani, Kanazawa (JP); Jiro Nakayama, Fukuoka (JP); Takahisa Matsufuji, Fukuoka (JP); Ravindra Pal Singh, Fukuoka (JP); Kenichi Okubo, Fukuoka (JP); Miki Kamikawa, Fukuoka (JP); Motomichi Takahashi, Tokyo (JP); Kentaro Oka, Tokyo (JP)

(73) Assignee: MIYARISAN PHARMACEUTICAL CO., LTD., Nagano (JP)

( * ) Notice: Subject to any disclaimer, the term of this patent is extended or adjusted under 35 U.S.C. 154(b) by 0 days.

(21) Appl. No.: 15/116,922

(22) PCT Filed: Feb. 4, 2015

(86) PCT No.: PCT/JP2015/053145
§ 371 (c)(1),
(2) Date: Aug. 5, 2016

(87) PCT Pub. No.: WO2015/119170
PCT Pub. Date: Aug. 13, 2015

(65) Prior Publication Data
US 2016/0355549 A1 Dec. 8, 2016

(30) Foreign Application Priority Data

Feb. 7, 2014 (JP) .................................. 2014-022811
Oct. 16, 2014 (JP) .................................. 2014-211962

(51) Int. Cl.
| C07K 7/06 | (2006.01) |
| A23L 33/18 | (2016.01) |
| A61K 38/00 | (2006.01) |
| A23K 20/147 | (2016.01) |
| A61K 35/74 | (2015.01) |
| C07K 7/64 | (2006.01) |

(52) U.S. Cl.
CPC .............. *C07K 7/06* (2013.01); *A23K 20/147* (2016.05); *A23L 33/18* (2016.08); *A61K 35/74* (2013.01); *C07K 7/64* (2013.01); *A61K 38/00* (2013.01)

(58) Field of Classification Search
None
See application file for complete search history.

(56) References Cited

U.S. PATENT DOCUMENTS

| 6,110,747 A | 8/2000 | Blaschuk et al. |
| 6,664,367 B1 | 12/2003 | Rajagopalan et al. |
| 2003/0166138 A1 | 9/2003 | Kinsella et al. |
| 2005/0203025 A1 | 9/2005 | Blaschuk et al. |
| 2009/0305955 A1 | 12/2009 | Monboisse et al. |
| 2010/0291093 A1 | 11/2010 | Janda et al. |
| 2014/0256615 A1 | 9/2014 | Blackwell et al. |

FOREIGN PATENT DOCUMENTS

| JP | 6-92862 A | 4/1994 |
| JP | 10503205 A | 3/1998 |
| JP | 2002509073 A | 3/2002 |
| JP | 2011500814 A | 1/2011 |
| JP | 2012180315 A | 9/2012 |
| JP | 2013227250 A | 11/2013 |
| WO | 9836050 A1 | 8/1998 |
| WO | 2003072034 A2 | 9/2003 |

OTHER PUBLICATIONS

Li et al. 2009 (Synthesis of cyclic peptides through direct aminolysis of peptide thioesters catalyzed by imidazole in aqueous organic solutions; Journal of Combinatorial Chemistry 11(6): 1066-1072).*
Laing, T.C. Antibody binding to a peptide but not the whole protein by recognition of the C-terminal carboxy group, Archives of Biochemistry and Biophysics, vol. 329, No. 2, pp. 208-214.*
Adessi and Soto, Converting a Peptide into a Drug: Strategies to Improve Stability and Bioavailability Current Medicinal Chemistry, 2002, 9, 963-978.*
Extended European Search Report of European Patent Application No. EP 15746797 dated May 19, 2017.
Y Tal-Gan et al. "Structural characterization of native autoinducing peptides and abiotic analogues reveals key features essential for activation and inhibition of AgrC quorum sensing receptor in *Staphylococcus aureus*", Journal of The American Chemical Society, vol. 135, Nov. 12, 2013(Nov. 12, 2013), pp. 18436-19444, XP002769976.
G J Lyon et al. "Key determinants of receptor activation in the agr autoinducing peptides of *Staphylococcus aureus*", Biochemistry, vol. 41,No.31,2002, pp. 10095-10104, XP 002769977.

(Continued)

*Primary Examiner* — Thomas S Heard

(74) *Attorney, Agent, or Firm* — Joseph G. Chu; JCIP

(57) ABSTRACT

To provide a means for preventing, treating and/or controlling health damages, including food poisoning and infections, caused by a bacterium belonging to the genus *Clostridium*.

The above object can be solved by a cyclic peptide containing the sequence Cys-Phe-Trp-Ala-His and/or a broth of *Clostridium butyricum*.

15 Claims, 7 Drawing Sheets

Specification includes a Sequence Listing.

(56) References Cited

OTHER PUBLICATIONS

Shimizu Tohru, Japanese journal of bacteriology (2004), 59 (2), pp. 377-385.

Ohtani, K., et al., Virulence Gene Regulation by the agr System in Clostridium perfringens, Journal of Bacteriology (2009), 191, pp. 3919-3927.

Sebaihia, M., et al., Genome sequence of a proteolytic (Group I) Clostridium botulinum strain Hall A and comparative analysis of the clostridial genomes, Genome Research (2007), 17, pp. 1082-1092.
Cooksley, C. M. et al., Regulation of neurotoxin production and sporulation by a putative agrBD signaling system in proteolytic Clostridium botulinum, Applied and Environmental Microbiology, 2010, vol. 76, No. 33, p. 4448-4460.
Synthesis of Cyclic Peptides through direct aminolysis of peptide thioesters catalyzed by imidazole in aqueous organic solutions, Li, Y. et. al., Journal of Combinatorial Chemistry, 2009, vol. 11, No. 6, p. 1066-1072.
Cyclization of all-L-Pentapeptides by Means of 1-Hydroxy-7-azabenzotriazole-Deroved Uronium and Phosphonium Reagents, Ehrlich, A. et. al. Journal of Organic Chemistry, 1996, vol. 61, No. 25, p. 8831-8838.
Zhang, L. and Tam, J. P., Synthesis and Application of Unprotected Cyclic Peptides as Building Blocks for Peptide Dendrimers, Journal of the American Chemical Society, 1997, vol. 119, No. 10, p. 2363-2370.
Vidal, J. E. et al., Evidence that the Agr-like quorum sensing system regulates the toxin production, cytotoxicity and pathogenicity of Clostridium perfringens type C isolate CN3685, Molecular microbiology, 2012, vol. 83, No. 1, p. 179-194.
Steiner, E. et al., An agr quorum sensing system that regulates granulose formation and sporulation in Clostridium acetobutylicum, Applied and Environmental Microbiology, 2012, vol. 78, No. 4, p. 1113-1122.
Sturme, M. H. J. et al., An agr-like two-component regulatory system in Lactobacillus plantarum is involved in production of a novel cyclic peptide and regulation of adherence, Journal of Bacteriology, 2005, vol. 187, No. 15, p. 5224-5235.
Tal-Gan, Y. et al., Highly Potent Inhibitors of Quorum Sensing in *Staphylococcus aureus* Revealed Through a Systematic Synthetic Study of the Group-III Autoinducing Peptide, Journal of the American Chemical Society, 2013, vol. 135, No. 21, p. 7869-7882.
George, E. A. et al., Cyclic peptide inhibitors of *Staphylococcal* virulence prepared by Fmoc-based thiolactone peptide synthesis, Journal of the American Chemical Society, 2008, vol. 130, No. 14, p. 4914-4924.
Zheng, J.-S.et al., Synthesis of Cyclic Peptides and Cyclic Proteins via Ligation of Peptide Hydrazides, ChemBioChem, 2012, vol. 13, No. 4, p. 542-546.
Kojima, Y. et al., Solid-phase synthesis and biological activity of malformin C and its derivatives, The Journal of Antibiotics, 2009, vol. 62, No. 12, p. 681-686.
Miao, Z. and Tam, J. P., Dehydropeptides from Orthogonal Ligation of Unprotected Peptides, Organic Letters, 2000, vol. 2, No. 23, p. 3711-3713.
Fukami, T. et al., Structure-Activity Relationships of Cyclic Pentapeptide Endothelin A Receptor Antagonists, Journal of Medicinal Chemistry, 1995, vol. 38, No. 21, p. 4309-24.
Isono, K. and Curtis, R. W., Chemical studies on malformin-II. Synthesis of cyclic pentapeptides related to malformin A, Phytochemistry, 1964, vol. 3, No. 2, p. 277-87.
Woo, T. D. H. et al., Inhibition of the cytotoxic effect of Clostridium difficile in vitro by Clostridium butyricum MIYAIRI 588 strain, Journal of Medical Microbiology, 2011, vol. 60, p. 1617-1625.
International Search Report & Written Opinion; International Preliminary Report on Patentability.

* cited by examiner

[FIG. 1]
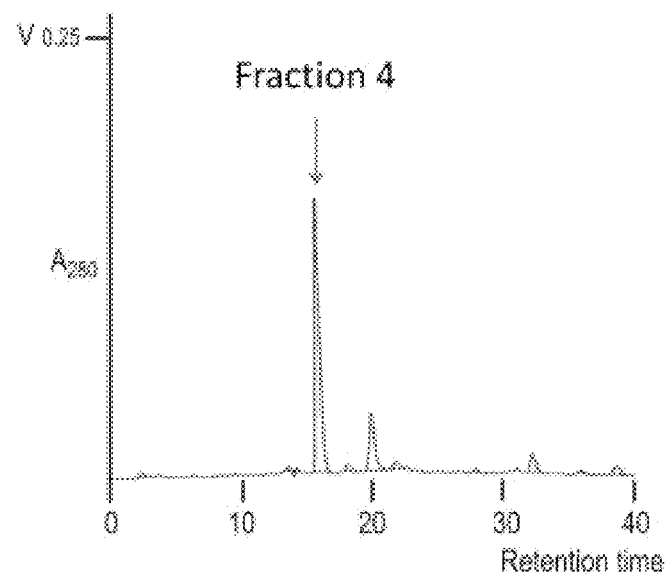
[FIG. 2]
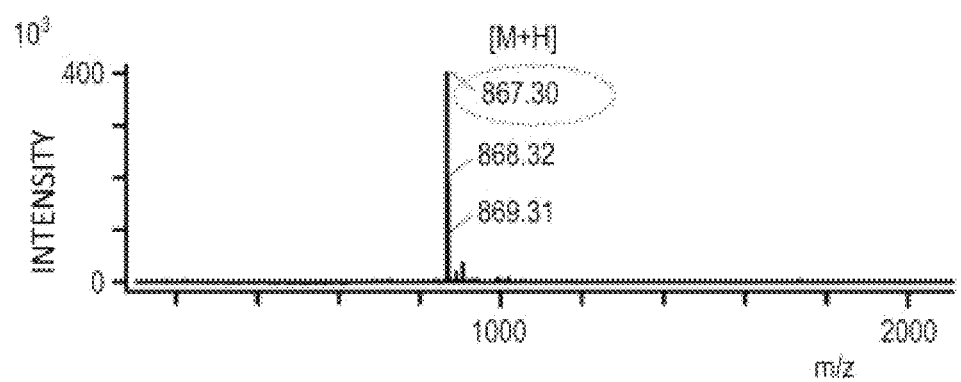

[FIG. 3]
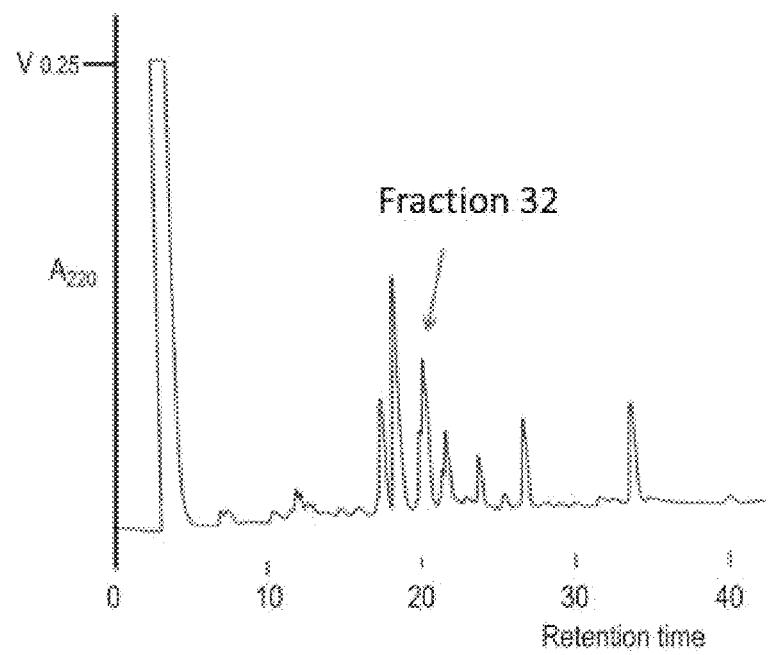
[FIG. 4]
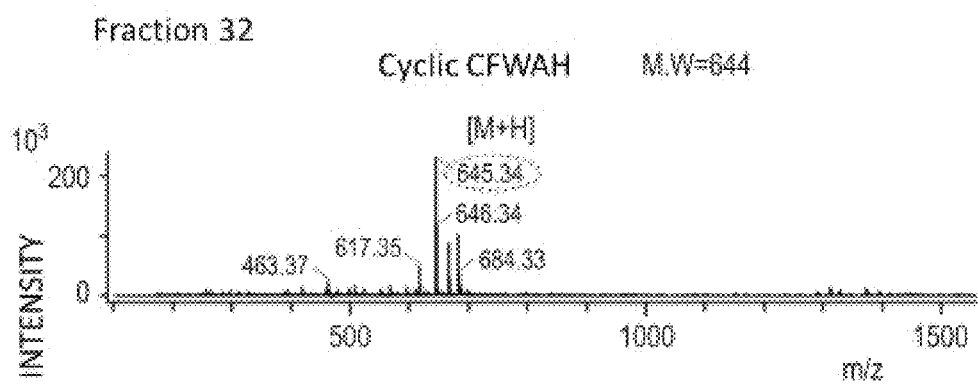

[FIG. 5]
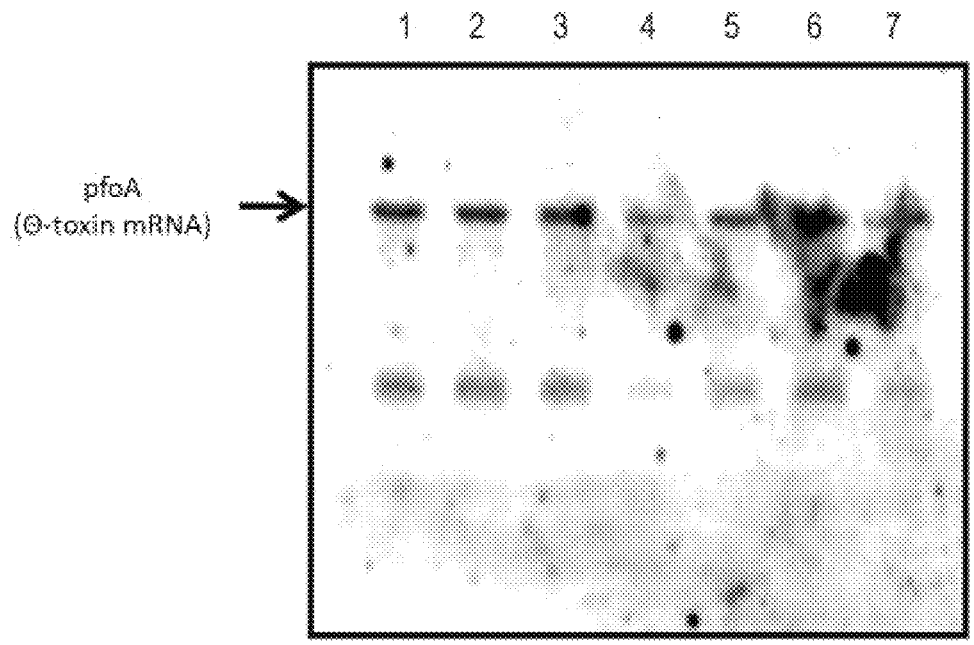
[FIG. 6]
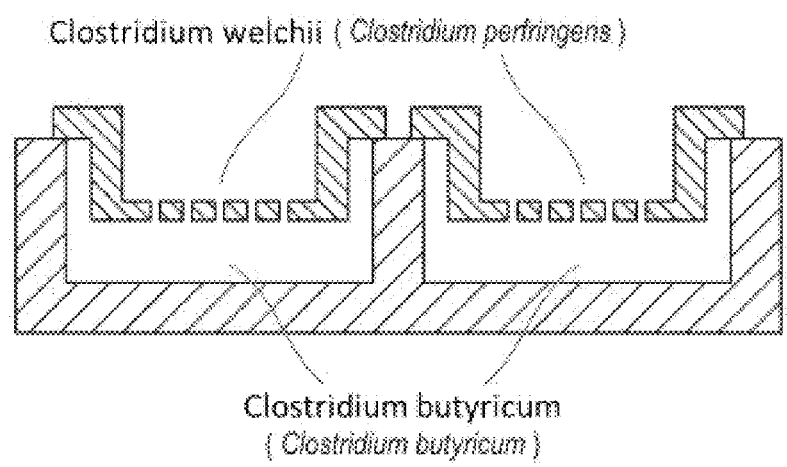

[FIG. 7]
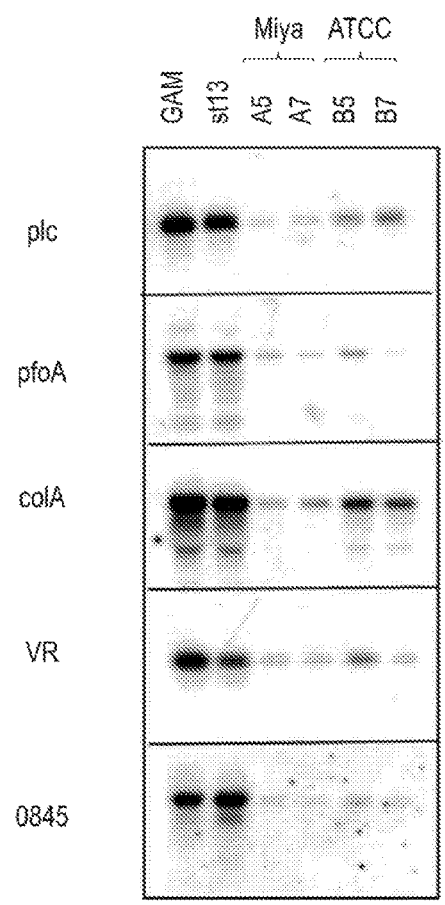

[FIG. 8]
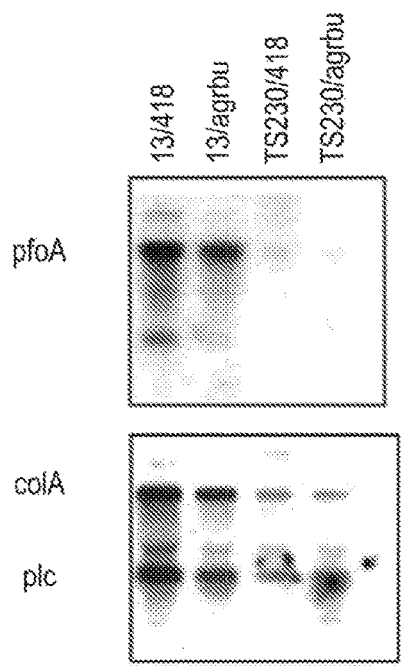
[FIG. 9]
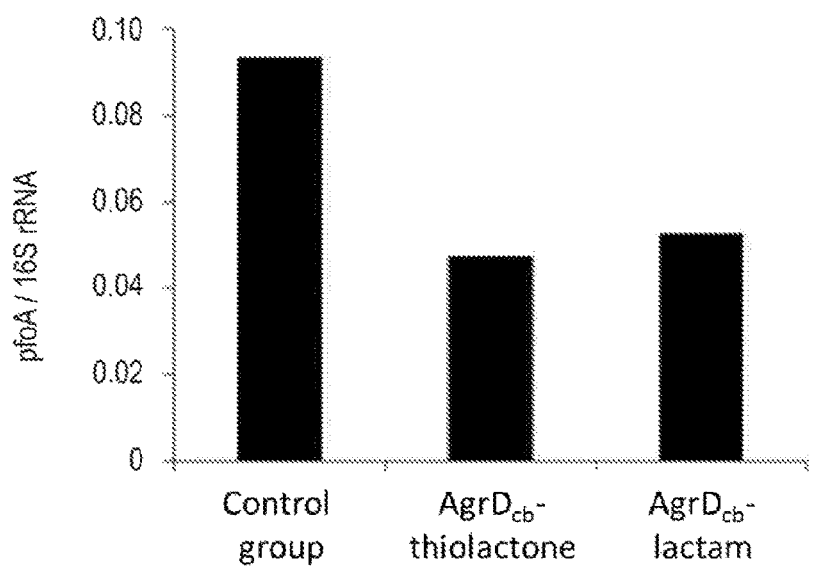

[FIG. 10]
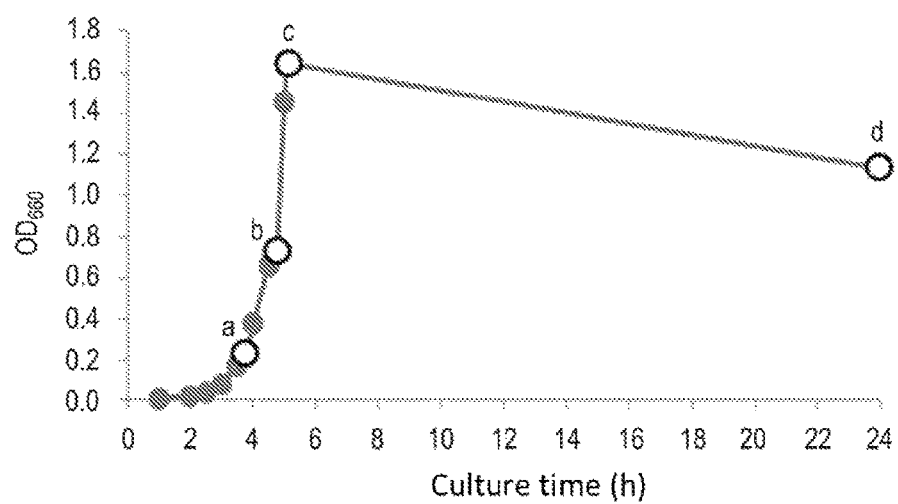

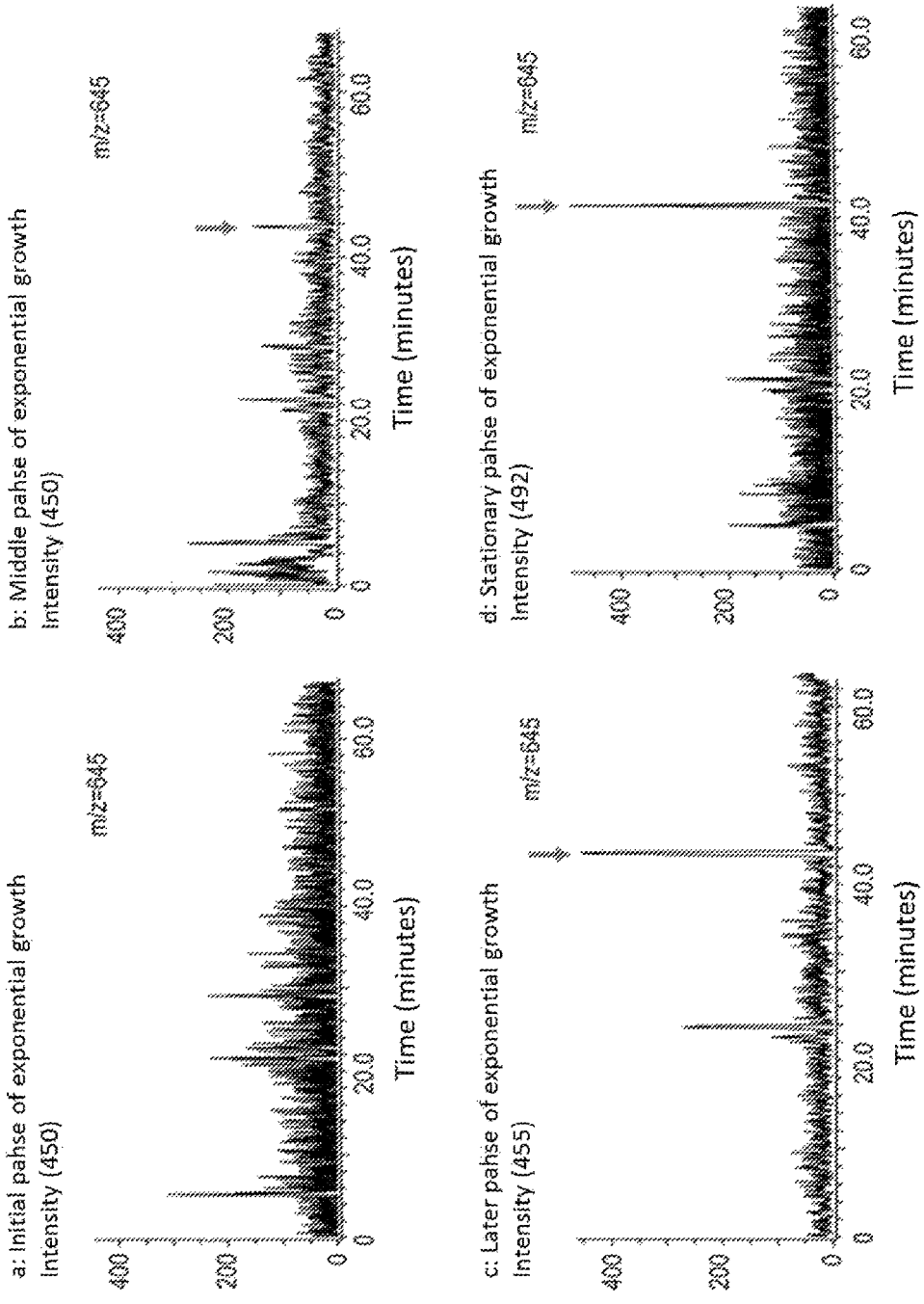
[FIG. 11]

PEPTIDE HAVING ACTIVITY OF INHIBITING PRODUCTION OF TOXIN BY BACTERIUM BELONGING TO GENUS CLOSTRIDIUM

A sequence listing under 37 CFR 1.821 as an ASCII text file is submitted herewith, the content of which is incorporated by reference in its entirety. The ASCII text file is entitled 00049WO01 SEQUENCELISTING with a date of creation of Jan. 23, 2015 (last accessed Jun. 30, 2016) and a size of 9.642 bytes.

TECHNICAL FIELD

The present invention relates to a peptide and a toxin production inhibitor for a bacterium belonging to the genus *Clostridium* by using the peptide. The present invention also relates to a toxin production inhibitor for a bacterium belonging to the genus *Clostridium* using a broth of *Clostridium butyricum*.

BACKGROUND ART

The bacterium belonging to the genus *Clostridium* is an anaerobic microbe and widely found in nature including soil, river, sea water, and intestine of a living organism, and it is also known as a bacterium which causes food poisoning or infectious diseases.

*Clostridium welchii* (*Clostridium perfringens*) as one type of the bacteria belonging to the genus *Clostridium* is also one of the bacteria, which cause food poisoning or an infectious disease. *Clostridium welchii* secretes various kinds of toxins and it is also known to cause gas gangrene, which is a lethal infection. Examples of toxins that are known to be secreted by *Clostridium welchii* include such as alpha-toxin (phospholipase C, name of the gene: plc), theta-toxin (hemolysin, name of the gene: pfoA), and kappa-toxin (collagenase, name of the gene: colA).

In Non-Patent Literature 1, it is described that, in *Clostridium welchii*, production of those toxins are positively regulated at gene level by a regulation system that is referred to as VirR/VirS system.

In response to an outer environment, gram-positive bacteria including those belonging to the genus *Clostridium* secrete an auto-inducer. A secreted autoinducer has an activity on a bacterium and promotes the production of a toxin. In *Staphylococcus aureus* as a gram-positive bacterium, a certain kind of peptide having a thiolactone structure functions as an autoinducer, and it is known to promote production of a toxin through the AgrA/AgrC system. In Non-Patent Literature 2, it is described that *Clostridium welchii* carries a homolog of the autoinducer peptide of *Staphylococcus aureus* and the homolog promotes production of a toxin through the VirR/VirS system.

In Non-Patent Literatures 3 and 4, it is described that *Clostridium difficile* and *Clostridium botulinum*, which are the bacterium belonging to the genus *Clostridium*, have a gene encoding the homolog of VirR and VirS.

In Non-Patent Literature 3, it is described that a bacterium belonging to the genus *Clostridium* such as *Clostridium welchii* (*Clostridium perfringens*), *Clostridium difficile*, botulinus (*Clostridium botulinum*) and *Clostridium acetobutylicum* has a gene encoding an autoinducer peptide AgrD.

CITATION LIST

Non-Patent Literatures

Non-Patent Literature 1: Shimizu Tohru, Japanese journal of bacteriology (2004), 59 (2), pages 377-385

Non-Patent Literature 2: Ohtani, K., et al., Journal of Bacteriology (2009), 191, pages 3919-3927

Non-Patent Literature 3: Sebaihia, M., et al., Genome Research (2007), 17, pages 1082-1092

Non-Patent Literature 4: Cooksley, C. M., et al., Applied and Environmental Microbiology (2010), 76, pages 4448-4460

SUMMARY OF INVENTION

The bacterium belonging to the genus *Clostridium* is a bacterium that causes food poisoning or a lethal infection, and thus development of a technique for preventing and controlling health damages induced by a bacterium belonging to the genus *Clostridium* is strongly desired.

A means for inhibiting the proliferation of a bacterium belonging to the genus *Clostridium* by using an antibiotic material has been also employed, but there is a problem of emergence of resistant bacteria against the antibiotics.

Thus, the present invention is devised in view of the above circumstances, and an object thereof is to provide a means for preventing, treating, and/or controlling health damages including such as food poisoning and infectious diseases that are caused by a bacterium belonging to the genus *Clostridium*.

The inventors of the present invention surprisingly found that, according to co-culture of *Clostridium butyricum* and a bacterium belonging to the genus *Clostridium*, production of a toxin by the bacterium belonging to the genus *Clostridium* can be inhibited. Based on such result, the inventors carried out intensive studies on a component that can inhibit the production of a toxin by a bacterium belonging to the genus *Clostridium*. As a result, it was found that, by using a peptide with a certain kind of structure, the aforementioned problems can be solved, and the present invention is completed accordingly. The present invention can be summarized as described below.

(1) A peptide represented by the following Formula (1):

[Chem. 1]

$$R^1-NH-\underset{S}{\overset{}{Cys}}-X^1\underset{X^4-X^3}{\overset{X^2}{\diagdown}}\quad(1)$$

in Formula (1), $R^1$ is selected from the group consisting of a hydrogen atom, an amino acid and a derivative thereof, and, with or without substituent(s), an acyl group having 1 to 10 carbon atoms, a benzyloxycarbonyl group, a 9-fluorenylmethyloxycarbonyl group and a phenylisothiocyanate group, $X^1$ and $X^2$ are each independently selected from the group consisting of Ala, Gly, Trp, Met, Pro, Phe, Val, Leu, Ile, and Tyr, and $X^3$ and $X^4$ are any amino acid, with the proviso that, when $X^2$ is Phe, $X^4$ is Thr, when $X^4$ is Ala, $X^1$ is Ala, and when $X^4$ is Thr, $X^3$ is Trp or Ala.

(2) A peptide represented by the following Formula (2):

[Chem. 2]

$$R^2-N\underset{O}{\overset{Z-X^5}{\diagdown}}\underset{X^8-X^7}{\overset{X^6}{\diagdown}}\quad(2)$$

in Formula (2), $R^2$ is selected from the group consisting of a hydrogen atom, an amino acid and a derivative thereof, and, with or without substituent(s), an acyl group having 1 to 10 carbon atoms, a benzyloxycarbonyl group, a 9-fluorenylmethyloxycarbonyl group and a phenylisothiocyanate group, $X^5$ and $X^6$ are each independently selected from the group consisting of Ala, Gly, Trp, Met, Pro, Phe, Val, Leu, Ile, and Tyr, $X^7$ and $X^8$ are any amino acid, and Z is selected from the group consisting of Cys, Ser, Thr, Tyr, Asn, and Gln, with the proviso that, when $X^6$ is Phe, $X^8$ is Thr, when $X^8$ is Ala, $X^5$ is Ala, and when $X^8$ is Thr, $X^7$ is Trp or Ala.

(3) A toxin production inhibitor for a bacterium belonging to the genus Clostridium including, as an effective ingredient, a cultured broth of Clostridium butyricum (Clostridium butyricum) or a dried product of the broth.

BRIEF DESCRIPTION OF DRAWINGS

FIG. 1 is a chromatogram of a cyclized synthetic peptide purified by reverse phase HPLC.

FIG. 2 is an MS spectrum in which the fraction 4 of FIG. 1 was analyzed.

FIG. 3 is a chromatogram of a synthetic peptide purified by reverse phase HPLC, in which the N-terminal protecting group (Fmoc) has been removed.

FIG. 4 is an MS spectrum in which the fraction 32 of FIG. 3 was analyzed.

FIG. 5 illustrates a result of determining gene expression of theta-toxin of Clostridium welchii using the peptide according to the present invention. It is illustrated that the cyclic CFWAH (lane 4) and the peptide 6n (lane 5) have an inhibitory activity on the production of a toxin by Clostridium welchii.

FIG. 6 is a drawing illustrating the plate used for co-culture test and scheme of the test.

FIG. 7 illustrates a result of Northern blot for determining the expressed amounts of toxin genes in Clostridium welchii when Clostridium butyricum and Clostridium welchii were co-cultured. It is shown that, due to a component secreted by Clostridium butyricum in the medium, the expression of the toxin genes in Clostridium welchii is inhibited.

FIG. 8 illustrates a result of Northern blot for determining the expressed amounts of toxin genes in Clostridium welchii in which the agrD gene of Clostridium butyricum has been expressed.

FIG. 9 illustrates a result of quantitative PCR for determining the inhibitory activity of $AgrD_{cb}$-thiolactone and $AgrD_{cb}$-lactam on the production of a toxin by Clostridium welchii.

FIG. 10 illustrates a variation in OD value during the culture of Example 5.

FIG. 11 illustrates a result of Example 5 analysed by ESI-MS.

DESCRIPTION OF EMBODIMENTS

Unlike an antibiotics that has been conventionally used for preventing/controlling food poisoning or an infectious diseases caused by a bacterium belonging to the genus Clostridium, the present invention inhibits the production of toxin by a bacterium belonging to the genus Clostridium. Thus, it is advantageous in that resistant bacteria are not likely to emerge. Hereinbelow, embodiments of the present invention are described. Meanwhile, the present invention is not limited to the following embodiments. Furthermore, the size ratio in the drawings is exaggerated for the sake of description, and it may be different from the actual ratio.

Furthermore, as described herein, the expression "X to Y" representing a range means "X or more and Y or less", and "weight" and "mass", "% by weight" and "% by mass", and "parts by weight" and "parts by mass" are treated as synonyms, respectively. Furthermore, unless specified otherwise, operations and measurement of a physical property or the like are carried out under conditions of room temperature (20 to 25° C.)/40 to 50% of relative humidity.

According to the present invention, health damages such as food poisoning or an infection induced by a bacterium belonging to the genus Clostridium can be prevented, treated, and/or controlled. The peptide according to the present invention is particularly effective for the prevention, treatment, and/or control of health damages induced by Clostridium welchii. Furthermore, by using a preparation according to the present invention that contains a cultured broth of Clostridium butyricum or a dried product of the broth as an effective ingredient, production of toxin by a bacterium belonging to the genus Clostridium can be inhibited.

[Peptide]

According to the first aspect, a peptide represented by the following Formula (1):

[Chem. 3]

$$R^1-NH-Cys-X^1\begin{matrix}\\S\\\\O\end{matrix}\begin{matrix}X^2\\|\\X^3\\X^4\end{matrix} \quad (1)$$

is provided.

In the specification, unless described specifically otherwise, the term "amino acid" indicates an α-amino acid which may be either D form or L form. However, it is preferably an α-amino acid of L form.

The nitrogen atom and hydrogen atom in Formula (1) are derived from an amino group of a cysteine residue. In Formula (1), the carbonyl group is derived from a carboxyl group of $X^4$. The sulfur atom in Formula (1) is derived from a thiol group of a cysteine residue. In Formula (1), the thiol group of a cysteine residue and the carboxyl group of $X^4$ are cyclized to form a thiolactone.

In Formula (1), $R^1$ is selected from the group consisting of a hydrogen atom, an amino acid and a derivative thereof, and, substituted or non-substituted, an acyl group having 1 to 10 carbon atoms, a benzyloxycarbonyl group (Z group), a 9-fluorenylmethyloxycarbonyl group (Fmoc group) and a phenylisothiocyanate group. Meanwhile, the benzyloxycarbonyl group (Z group) and 9-fluorenylmethyloxycarbonyl group (Fmoc group) are representative groups for protecting an amino group, which are universally used for peptide synthesis. Furthermore, the phenylisothiocyanate group is a group, which is formed by a reaction between phenylisothiocyanate and an amino group of an amino acid, and is universally used for amino acid sequencing. When $R^1$ is an amino acid or a derivative thereof, a peptide bond is formed between the carbon atom of a carboxy group of $R^1$ and the nitrogen atom of Formula (1).

Examples of the "amino acid derivative" include ornithine, sarcosine, desmosine, isodesmosine, hydroxylysine, 3-hydroxyproline, 4-hydroxyproline, 2-aminoadipic acid, 3-aminoadipic acid, β-alanine, β-aminopropionic acid, 2-aminobutyric acid, 4-aminobutyric acid, 6-aminocapronic acid, 2-aminoheptanoic acid, 2-aminoisobutyric acid, and 3-aminoisobutyric acid. The acyl group is a saturated or unsaturated and linear or branched group with 1 to 10 carbon atoms. Specific examples thereof include a formyl group, an acetyl group, a propionyl group, a butyryl group, an isobutyryl group, a barenyl group, an isobarenyl group, a pyvaloyl group, a hexanoyl group, an octanoyl group, an acryloyl group, and a methacryloyl group, but not limited thereto.

With regard to $R^1$ in Formula (1), a substituent group for an acyl group, a benzyloxycarbonyl group, a 9-fluorenylmethyloxycarbonyl group, and a phenylisothiocyanate group is not particularly limited as long as the effect of the present invention is obtained, and any substituent group may be employed. Examples thereof include aliphatic hydrocarbon groups such as a methyl group, an ethyl group, a n-propyl group, an isopropyl group, a n-butyl group, an isobutyl group, a sec-butyl group, a tert-butyl group, a n-pentyl group, an isopentyl group, a neopentyl group, a n-hexyl group, a n-heptyl group, a n-octyl group, or a 2-ethylhexyl group; alicyclic hydrocarbon groups such as a cyclopropyl group, a cyclopentyl group, or a cyclohexyl group; aromatic hydrocarbon groups such as a phenyl group; a hydroxyl group; alkoxy groups such as a methoxy group or an ethoxy group; alkexnyloxy groups such as an allyloxy group; aryloxy groups such as a phenoxy group; aralkyloxy groups such as a benzyloxy group; acyloxy groups such as an acetyloxy group or a propionyloxy group; a carboxyl group; acyl groups such as an acetyl group, a propionyl group, or a benzoyl group; an oxo group; halogen atoms such as a fluorine atom, a chlorine atom, or a chlorine atom.

$R^1$ in Formula (1) is preferably selected from the group consisting of a hydrogen atom, Ala, Gly, Trp, Met, Pro, Phe, Val, Leu, Ile, and a benzyloxycarbonyl group, and it is more preferably a hydrogen atom or a benzyloxycarbonyl group.

With regard to Formula (1), it is preferable that $R^1$ is selected from the group consisting of a hydrogen atom, Ala, Gly, Trp, Met, Pro, Phe, Val, Leu, Ile, and a benzyloxycarbonyl group, $X^1$ and $X^2$ are each independently selected from the group consisting of Ala, Gly, Trp, Met, Pro, Phe, Val, Leu, Ile, and Tyr, $X^3$ is selected from the group consisting of Ala, Gly, Trp, Met, Pro, Phe, Val, Leu, and Ile, and $X^4$ is any amino acid, with the proviso that, when $X^2$ is Phe, $X^4$ is Thr, when $X^4$ is Ala, $X^1$ is Ala, and when $X^4$ is Thr, $X^3$ is Trp or Ala.

With regard to Formula (1), $X^1$ is selected from the group consisting of Ala, Gly, Trp, Met, Pro, Phe, Val, Leu, Ile, and Tyr, but it is preferably selected from the group consisting of Phe, Trp, Tyr, Ala, Val, Leu, and Ile. Thus, according to one embodiment of the present invention, $R^1$ is selected from the group consisting of a hydrogen atom, Ala, Gly, Trp, Met, Pro, Phe, Val, Leu, Ile, and a benzyloxycarbonyl group, $X^1$ is selected from the group consisting of Phe, Trp, Tyr, Ala, Val, Leu, and Ile, $X^2$ is selected from the group consisting of Ala, Gly, Trp, Met, Pro, Phe, Val, Leu, Ile, and Tyr, $X^3$ is selected from the group consisting of Ala, Gly, Trp, Met, Pro, Phe, Val, Leu, and Ile, and $X^4$ is any amino acid, with the proviso that, when $X^2$ is Phe, $X^4$ is Thr, when $X^4$ is Ala, $X^1$ is Ala, and when $X^4$ is Thr, $X^3$ is Trp or Ala. In Formula (1), $X^1$ is more preferably selected from the group consisting of Phe, Leu, and Ala. Thus, according to one embodiment of the present invention, $R^1$ is a hydrogen atom or a benzyloxycarbonyl group, $X^1$ is selected from the group consisting of Phe, Leu, and Ala, $X^2$ is selected from the group consisting of Ala, Gly, Trp, Met, Pro, Phe, Val, Leu, Ile and Tyr, $X^3$ is selected from the group consisting of Ala, Gly, Trp, Met, Pro, Phe, Val, Leu, and Ile, and $X^4$ is any amino acid, with the proviso that, when $X^2$ is Phe, $X^4$ is Thr, when $X^4$ is Ala, $X^1$ is Ala, and when $X^4$ is Thr, $X^3$ is Trp or Ala.

With regard to Formula (1), $X^2$ is selected from the group consisting of Ala, Gly, Trp, Met, Pro, Phe, Val, Leu, Ile, and Tyr, but it is preferably selected from the group consisting of Phe, Trp, and Tyr. Thus, according to one embodiment of the present invention, $R^1$ is selected from the group consisting of a hydrogen atom, Ala, Gly, Trp, Met, Pro, Phe, Val, Leu, Ile, and a benzyloxycarbonyl group, $X^1$ is selected from the group consisting of Ala, Gly, Trp, Met, Pro, Phe, Val, Leu, Ile, and Tyr, $X^2$ is selected from the group consisting of Phe, Trp, and Tyr, $X^3$ is selected from the group consisting of Ala, Gly, Trp, Met, Pro, Phe, Val, Leu, and Ile, and $X^4$ is any amino acid, with the proviso that, when $X^2$ is Phe, $X^4$ is Thr, when $X^4$ is Ala, $X^1$ is Ala, and when $X^4$ is Thr, $X^3$ is Trp or Ala. With regard to Formula (1), it is more preferable that $X^2$ is Phe or Trp. Thus, according to one embodiment of the present invention, R' is a hydrogen atom or a benzyloxycarbonyl group, $X^1$ is selected from the group consisting of Phe, Trp, Tyr, Ala, Val, Leu, and Ile, $X^2$ is Phe or Trp, $X^3$ is selected from the group consisting of Ala, Gly, Trp, Met, Pro, Phe, Val, Leu, and Ile, and $X^4$ is any amino acid, with the proviso that, when $X^2$ is Phe, $X^4$ is Thr, when $X^4$ is Ala, $X^1$ is Ala, and when $X^4$ is Thr, $X^3$ is Trp or Ala.

With regard to Formula (1), $X^3$ is any amino acid, and it is preferably selected from the group consisting of Ala, Gly, Trp, Met, Pro, Phe, Val, Leu, and Ile, and more preferably selected from the group consisting of Ala, Trp, and Phe. Thus, according to one embodiment of the present invention, $R^1$ is selected from the group consisting of a hydrogen atom, Ala, Gly, Trp, Met, Pro, Phe, Val, Leu, Ile, and a benzyloxycarbonyl group, $X^1$ and $X^2$ are each independently selected from the group consisting of Ala, Gly, Trp, Met, Pro, Phe, Val, Leu, Ile, and Tyr, $X^3$ is selected from the group consisting of Ala, Trp, and Phe, and $X^4$ is any amino acid, with the proviso that, when $X^2$ is Phe, $X^4$ is Thr, when $X^4$ is Ala, $X^1$ is Ala, and when $X^4$ is Thr, $X^3$ is Trp or Ala. According to other embodiment, $R^1$ is selected from the group consisting of a hydrogen atom, Ala, Gly, Trp, Met, Pro, Phe, Val, Leu, Ile, and a benzyloxycarbonyl group, $X^1$ is selected from the group consisting of Phe, Trp, Tyr, Ala, Val, Leu, and Ile, $X^2$ is selected from the group consisting of Phe, Trp, and Tyr, $X^3$ is selected from the group consisting of Ala, Trp, and Phe, and $X^4$ is any amino acid, with the proviso that, when $X^2$ is Phe, $X^4$ is Thr, when $X^4$ is Ala, $X^1$ is Ala, and when $X^4$ is Thr, $X^3$ is Trp or Ala.

With regard to Formula (1), $X^4$ is any amino acid, and it may be selected from the group consisting of His, Lys, Arg, Ala, Thr, and Ser. Thus, in Formula (1), $R^1$ is selected from the group consisting of a hydrogen atom, Ala, Gly, Trp, Met, Pro, Phe, Val, Leu, Ile, and a benzyloxycarbonyl group, $X^1$ and $X^2$ are each independently selected from the group consisting of Ala, Gly, Trp, Met, Pro, Phe, Val, Leu, Ile, and Tyr, $X^3$ is any amino acid, and $X^4$ is selected from the group consisting of His, Lys, Arg, Ala, Thr, and Ser, with the proviso that, when $X^2$ is Phe, $X^4$ is Thr, when $X^4$ is Ala, $X^1$ is Ala, and when $X^4$ is Thr, $X^3$ is Trp or Ala. More preferably, with regard to Formula (1), $R^1$ is a hydrogen atom or a benzyloxycarbonyl group, $X^1$ is selected from the group consisting of Phe, Trp, Tyr, Ala, Val, Leu, and Ile, $X^2$ is selected from the group consisting of Phe, Trp, and Tyr, $X^3$ is selected from the group consisting of Ala, Gly, Trp, Met, Pro, Phe, Val, Leu, and Ile, and $X^4$ is selected from the group consisting of His, Lys, Arg, Ala, Thr, and Ser, with the proviso that, when $X^2$ is Phe, $X^4$ is Thr, when $X^4$ is Ala, $X^1$ is Ala, and when $X^4$ is Thr, $X^3$ is Trp or Ala. Even more preferably, $X^4$ is selected from the group consisting of His, Ala, Thr, and Ser. Thus, according to one embodiment of the present invention, with regard to Formula (1), $R^1$ is a hydrogen atom or a benzyloxycarbonyl group, $X^1$ is selected from the group consisting of Phe, Trp, Tyr, Ala, Val, Leu, and Ile, $X^2$ is selected from the group consisting of Phe, Trp, and Tyr, $X^3$ is selected from the group consisting of Ala, Trp, and Phe, and $X^4$ is selected from the group consisting of His, Ala, Thr, and Ser, with the proviso that, when $X^2$ is Phe, $X^4$ is Thr, when $X^4$ is Ala, $X^1$ is Ala, and when $X^4$ is Thr, $X^3$ is Trp or Ala.

According to a more preferred embodiment of the present invention, with regard to Formula (1), $R^1$ is a hydrogen atom or a benzyloxycarbonyl group, $X^1$ is selected from the group consisting of Phe, Leu, and Ala, $X^2$ is Phe or Trp, $X^3$ is selected from the group consisting of Ala, Trp, and Phe, and $X^4$ is selected from the group consisting of His, Ala, Thr, and Ser, with the proviso that, when $X^2$ is Phe, $X^4$ is Thr, when $X^4$ is Ala, $X^1$ is Ala, and when $X^4$ is Thr, $X^3$ is Trp or Ala.

A sequence represented by SEQ ID NO: 1 in which $R^1$ is a hydrogen atom, $X^1$ is Phe, $X^2$ is Trp, $X^3$ is Ala, and $X^4$ is His in Formula (1) is particularly preferable.

Other than the above, a particularly preferred sequence of Formula (1) is given below as SEQ ID NOS: 20 to 22, 31, 33, and 35.

TABLE 1

| $R^1$ | $X^1$ | $X^2$ | $X^3$ | $X^4$ | SEQ ID NO |
|---|---|---|---|---|---|
| Benzyloxycarbonyl group | Ala | Trp | Ala | Ala | 33 |
| Benzyloxycarbonyl group | Ala | Trp | Phe | Ala | 20 |
| Hydrogen atom | Ala | Trp | Phe | Ala | 20 |
| Benzyloxycarbonyl group | Leu | Trp | Phe | Ser | 21 |
| Hydrogen atom | Leu | Trp | Phe | Ser | 21 |
| Benzyloxycarbonyl group | Leu | Phe | Trp | Thr | 22 |
| Hydrogen atom | Leu | Phe | Trp | Thr | 22 |
| Benzyloxycarbonyl group | Leu | Trp | Ala | Thr | 31 |
| Benzyloxycarbonyl group | Leu | Trp | Ala | Ser | 35 |

According to one embodiment of the present invention, a peptide represented by the following Formula (2) is provided:

[Chem. 4]

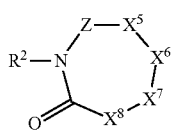

(2)

In Formula (2), $R^2$ is selected from the group consisting of a hydrogen atom, an amino acid and a derivative thereof, and, substituted or non-substituted, an acyl group having 1 to 10 carbon atoms, a benzyloxycarbonyl group (Z group), a 9-fluorenylmethyloxycarbonyl group (Fmoc group) and a phenylisothiocyanate group. $X^5$ and $X^6$ are each independently selected from the group consisting of Ala, Gly, Trp, Met, Pro, Phe, Val, Leu, Ile, and Tyr, $X^7$ and $X^8$ are any amino acid, and Z is selected from the group consisting of Cys, Ser, Thr, Tyr, Asn, and Gln, with the proviso that, when $X^6$ is Phe, $X^8$ is Thr, when $X^8$ is Ala, $X^5$ is Ala, and when $X^8$ is Thr, $X^7$ is Trp or Ala.

The carbonyl group in Formula (2) is derived from a carboxyl group of $X^8$. The nitrogen atom in Formula (2) is derived from an amino group of Z. In Formula (2), the nitrogen atom of Z and the carboxyl group of $X^8$ are cyclized to form a lactam which is either substituted (for a case where $R^2$ is not a hydrogen atom) or non-substituted (for a case where $R^2$ is a hydrogen atom).

In Formula (2), $R^2$ is selected from the group consisting of a hydrogen atom, an amino acid and a derivative thereof, and, with or without substituent(s), an acyl group having 1 to 10 carbon atoms, a benzyloxycarbonyl group (Z group), a 9-fluorenylmethyloxycarbonyl group (Fmoc group) and a phenylisothiocyanate group. When $R^2$ is an amino acid or a derivative thereof, carbon atom of the carboxy group of $R^2$ and nitrogen atom of Formula (2) form an amide bond.

The "derivative of amino acid" is as defined above for Formula (1). Furthermore, a substituent group for an acyl group, a benzyloxycarbonyl group, a 9-fluorenylmethyloxycarbonyl group, and a phenylisothiocyanate group in $R^2$ of Formula (2) is also as defined above for Formula (1).

With regard to Formula (2), $R^2$ is preferably selected from the group consisting of a hydrogen atom, Ala, Gly, Trp, Met, Pro, Phe, Val, Leu, Ile, and a benzyloxycarbonyl group, and more preferably a hydrogen atom or a benzyloxycarbonyl group.

With regard to Formula (2), $R^2$ is preferably selected from the group consisting of a hydrogen atom, Ala, Gly, Trp, Met, Pro, Phe, Val, Leu, Ile, and a benzyloxycarbonyl group, $X^5$ and $X^6$ are each independently selected from the group consisting of Ala, Gly, Trp, Met, Pro, Phe, Val, Leu, Ile, and Tyr, $X^7$ is selected from the group consisting of Ala, Gly, Trp, Met, Pro, Phe, Val, Leu, and Ile, $X^8$ is any amino acid, and Z is selected from the group consisting of Cys, Ser, Thr, Tyr, Asn, and Gln, with the proviso that, when $X^6$ is Phe, $X^8$ is Thr, when $X^8$ is Ala, $X^5$ is Ala, and when $X^8$ is Thr, $X^7$ is Trp or Ala.

With regard to Formula (2), $X^5$ is preferably selected from the group consisting of Phe, Trp, Tyr, Ala, Val, Leu, and Ile. Thus, according to one embodiment of the present invention, $R^2$ is selected from the group consisting of a hydrogen atom, Ala, Gly, Trp, Met, Pro, Phe, Val, Leu, Ile, and a benzyloxycarbonyl group, $X^5$ is selected from the group consisting of Phe, Trp, Tyr, Ala, Val, Leu, and Ile, $X^6$ is selected from the group consisting of Ala, Gly, Trp, Met, Pro, Phe, Val, Leu, Ile, and Tyr, $X^7$ is selected from the group consisting of Ala, Gly, Trp, Met, Pro, Phe, Val, Leu, and Ile, $X^8$ is any amino acid, and Z is selected from the group consisting of Cys, Ser, Thr, Tyr, Asn, and Gln, with the proviso that, when $X^6$ is Phe, $X^8$ is Thr, when $X^8$ is Ala, $X^5$ is Ala, and when $X^8$ is Thr, $X^7$ is Trp or Ala. With regard to Formula (2), it is more preferable that $X^5$ is selected from the group consisting of Phe, Leu, and Ala. Thus, according to one embodiment of the present invention, $R^2$ is selected from the group consisting of a hydrogen atom or a benzyloxycarbonyl group, $X^5$ is selected from the group consisting of Phe, Leu, and Ala, $X^6$ is selected from the group consisting of Ala, Gly, Trp, Met, Pro, Phe, Val, Leu, Ile, and Tyr, $X^7$ is selected from the group consisting of Ala, Gly, Trp, Met, Pro, Phe, Val, Leu, and Ile, $X^8$ is any amino acid, and Z is selected from the group consisting of Cys, Ser, Thr, Tyr, Asn, and Gln, with the proviso that, when $X^6$ is Phe, $X^8$ is Thr, when $X^8$ is Ala, $X^5$ is Ala, and when $X^8$ is Thr, $X^7$ is Trp or Ala.

With regard to Formula (2), $X^6$ is preferably selected from the group consisting of Phe, Trp, and Tyr. Thus, according to one embodiment of the present invention, $R^2$ is selected from the group consisting of a hydrogen atom, Ala, Gly, Trp, Met, Pro, Phe, Val, Leu, Ile, and a benzyloxycarbonyl group, $X^5$ is selected from the group consisting of Ala, Gly, Trp, Met, Pro, Phe, Val, Leu, Ile, and Tyr, $X^6$ is selected from the group consisting of Phe, Trp, and Tyr, $X^7$ is selected from the group consisting of Ala, Gly, Trp, Met, Pro, Phe, Val, Leu, and Ile, $X^8$ is any amino acid, and Z is selected from the group consisting of Cys, Ser, Thr, Tyr, Asn, and Gln, with the proviso that, when $X^6$ is Phe, $X^8$ is Thr, when $X^8$ is Ala, $X^5$ is Ala, and when $X^8$ is Thr, $X^7$ is Trp or Ala. With regard to Formula (2), $X^6$ is more preferably Phe or Trp. Thus, according to one embodiment of the present invention, $R^2$ is a hydrogen atom or a benzyloxycarbonyl group, $X^5$ is selected from the group consisting of Phe, Trp, Tyr, Ala, Val, Leu, and Ile, $X^6$ is Phe or Trp, $X^7$ is selected from the group consisting of Ala, Gly, Trp, Met, Pro, Phe, Val, Leu, and Ile, $X^8$ is any amino acid, and Z is selected from the group consisting of Cys, Ser, Thr, Tyr, Asn, and Gln, with the proviso that, when $X^6$ is Phe, $X^8$ is Thr, when $X^8$ is Ala, $X^5$ is Ala, and when $X^8$ is Thr, $X^7$ is Trp or Ala.

With regard to Formula (2), $X^7$ is any amino acid, and it is preferably selected from the group consisting of Ala, Gly, Trp, Met, Pro, Phe, Val, Leu, and Ile, and more preferably selected from the group consisting of Ala, Trp, and Phe. Thus, according to one embodiment of the present invention, $R^2$ is selected from the group consisting of a hydrogen atom, Ala, Gly, Trp, Met, Pro, Phe, Val, Leu, Ile, and a benzyloxycarbonyl group, $X^5$ and $X^6$ are each independently selected from the group consisting of Ala, Gly, Trp, Met, Pro, Phe, Val, Leu, Ile, and Tyr, $X^7$ is selected from the group consisting of Ala, Trp, and Phe, $X^8$ is any amino acid and, Z is selected from the group consisting of Cys, Ser, Thr, Tyr, Asn, and Gln, with the proviso that, when $X^6$ is Phe, $X^8$ is Thr, when $X^8$ is Ala, $X^5$ is Ala, and when $X^8$ is Thr, $X^7$ is Trp or Ala. According to other embodiment, $R^2$ is selected from the group consisting of a hydrogen atom, Ala, Gly, Trp, Met, Pro, Phe, Val, Leu, Ile, and a benzyloxycarbonyl group, $X^5$ is selected from the group consisting of Phe, Trp, Tyr, Ala, Val, Leu, and Ile, $X^6$ is selected from the group consisting of Phe, Trp, and Tyr, $X^7$ is selected from the group consisting of Ala, Trp, and Phe, $X^8$ is any amino acid, and Z is selected from the group consisting of Cys, Ser, Thr, Tyr, Asn, and Gln, with the proviso that, when $X^6$ is Phe, $X^8$ is Thr, when $X^8$ is Ala, $X^5$ is Ala, and when $X^8$ is Thr, $X^7$ is Trp or Ala.

With regard to Formula (2), $X^8$ may be selected from the group consisting of His, Lys, Arg, Ala, Thr, and Ser. Thus, in Formula (2), $R^2$ is selected from the group consisting of a hydrogen atom, Ala, Gly, Trp, Met, Pro, Phe, Val, Leu, Ile, and a benzyloxycarbonyl group, $X^3$ and $X^6$ are each independently selected from the group consisting of Ala, Gly, Trp, Met, Pro, Phe, Val, Leu, Ile, and Tyr, $X^7$ is any amino acid, $X^8$ is selected from the group consisting of His, Lys, Arg, Ala, Thr, and Ser, and Z is selected from the group consisting of Cys, Ser, Thr, Tyr, Asn, and Gln, with the proviso that, when $X^6$ is Phe, $X^8$ is Thr, when $X^8$ is Ala, $X^5$ is Ala, and when $X^8$ is Thr, $X^7$ is Trp or Ala. More preferably, with regard to Formula (2), $R^2$ is a hydrogen atom or a benzyloxycarbonyl group, $X^5$ is selected from the group consisting of Phe, Trp, Tyr, Ala, Val, Leu, and Ile, $X^6$ is selected from the group consisting of Phe, Trp, and Tyr, $X^7$ is selected from the group consisting of Ala, Gly, Trp, Met, Pro, Phe, Val, Leu, and Ile, $X^8$ is selected from the group consisting of His, Lys, Arg, Ala, Thr, and Ser, and Z is selected from the group consisting of Cys, Ser, Thr, Tyr, Asn, and Gln, with the proviso that, when $X^6$ is Phe, $X^8$ is Thr, when $X^8$ is Ala, $X^5$ is Ala, and when $X^8$ is Thr, $X^7$ is Trp or Ala. Even more preferably, $X^8$ is selected from the group consisting of His, Ala, Thr, and Ser. Thus, according to one embodiment of the present invention, in Formula (1), $R^2$ is a hydrogen atom or a benzyloxycarbonyl group, $X^5$ is selected from the group consisting of Phe, Trp, Tyr, Ala, Val, Leu, and Ile, $X^6$ is selected from the group consisting of Phe, Trp, and Tyr, $X^7$ is selected from the group consisting of Ala, Trp, and Phe, and $X^8$ is selected from the group consisting of His, Ala, Thr, and Ser, with the proviso that, when $X^6$ is Phe, $X^8$ is Thr, when $X^8$ is Ala, $X^5$ is Ala, and when $X^8$ is Thr, $X^7$ is Trp or Ala.

With regard to Formula (2), Z is preferably Cys. Thus, in Formula (2), $R^2$ is selected from the group consisting of a hydrogen atom, Ala, Gly, Trp, Met, Pro, Phe, Val, Leu, Ile, and a benzyloxycarbonyl group, $X^5$ and $X^6$ are each independently selected from the group consisting of Ala, Gly, Trp, Met, Pro, Phe, Val, Leu, Ile, and Tyr, $X^7$ and $X^8$ are any amino acid, and Z is Cys, with the proviso that, when $X^6$ is Phe, $X^8$ is Thr, when $X^8$ is Ala, $X^5$ is Ala, and when $X^8$ is Thr, $X^7$ is Trp or Ala. More preferably, $R^2$ is a hydrogen atom or a benzyloxycarbonyl group, $X^5$ is selected from the group consisting of Phe, Trp, Tyr, Ala, Val, Leu, and Ile, $X^6$ is selected from the group consisting of Phe, Trp, and Tyr, $X^7$ is selected from the group consisting of Ala, Trp, and Phe, $X^8$ is selected from the group consisting of His, Lys, Arg, Ala, Thr, and Ser, and Z is Cys, with the proviso that, when $X^6$ is Phe, $X^8$ is Thr, when $X^8$ is Ala, $X^5$ is Ala, and when $X^8$ is Thr, $X^7$ is Trp or Ala.

According to a more preferred embodiment of the present invention, with regard to Formula (2), $R^2$ is a hydrogen atom or a benzyloxycarbonyl group, $X^5$ is selected from the group consisting of Phe, Leu, and Ala, $X^6$ is Phe or Trp, $X^7$ is selected from the group consisting of Ala, Trp, and Phe, $X^8$ is selected from the group consisting of His, Ala, Thr, and Ser, and Z is Cys, with the proviso that, when $X^6$ is Phe, $X^8$ is Thr, when $X^8$ is Ala, $X^5$ is Ala, and when $X^8$ is Thr, $X^7$ is Trp or Ala.

A sequence represented by SEQ ID NO: 23 in which $R^2$ is a hydrogen atom, $X^5$ is Phe, $X^6$ is Trp, $X^7$ is Ala, $X^8$ is His, and Z is Cys in Formula (2) is particularly preferable.

Other than the above, a particularly preferred sequence of Formula (2) is given below as SEQ ID NOS: 24 to 26, 32, 34, and 36.

TABLE 2

| $R^2$ | Z | $X^5$ | $X^6$ | $X^7$ | $X^8$ | SEQ ID NO |
|---|---|---|---|---|---|---|
| Benzyloxycarbonyl group | Cys | Ala | Trp | Ala | Ala | 34 |
| Benzyloxycarbonyl group | Cys | Ala | Trp | Phe | Ala | 24 |
| Hydrogen atom | Cys | Ala | Trp | Phe | Ala | 24 |
| Benzyloxycarbonyl group | Cys | Leu | Trp | Phe | Ser | 25 |
| Hydrogen atom | Cys | Leu | Trp | Phe | Ser | 25 |
| Benzyloxycarbonyl group | Cys | Leu | Phe | Trp | Thr | 26 |
| Hydrogen atom | Cys | Leu | Phe | Trp | Thr | 26 |
| Benzyloxycarbonyl group | Cys | Leu | Trp | Ala | Thr | 32 |
| Benzyloxycarbonyl group | Cys | Leu | Trp | Ala | Ser | 36 |

It is known in the pertinent technical field that, based on a difference in side chain, each amino acid can be replaced with an amino acid with similar property (preservative replacement). Phe may be replaced with a non-polar amino acid such as Ala, Gly, Trp, Met, Pro, Val, Leu, or Ile, or with an aromatic amino acid such as Tyr, for example. Trp may be replaced with a non-polar amino acid such as Ala, Gly, Phe, Met, Pro, Val, Leu, or Ile, or with an aromatic amino acid such as Tyr, for example. Ala may be replaced with a non-polar amino acid such as Phe, Gly, Trp, Met, Pro, Val, Leu, Ile, for example. His may be replaced with a basic amino acid such as Lys or Arg, for example. Cys may be replaced with a polar amino acid with no charge such as Ser, Thr, Tyr, Asn, or Gln, for example.

Meanwhile, with regard to the peptide represented by Formula (1), when $X^4$ is Ala, $X^1$ is Ala, and when $X^4$ is Thr, $X^3$ is Trp or Ala. Furthermore, with regard to the peptide represented by Formula (2), when $X^8$ is Ala, $X^5$ is Ala, and when $X^8$ is Thr, $X^7$ is Trp or Ala. Thus, for a case where $X^4$ or $X^8$ is Ala or Thr, the aforementioned preservative replacement at a predetermined position in the peptide cannot be achieved as an exception. It may be due to the reason that binding to *Clostridium welchii* VirS is limited by the amino acid species of $X^4$ or $X^8$ which form a thiolactone structure with cysteine of Formula (1) or a lactam structure with Z of Formula (2). However, this mechanism is just assumption, and the technical scope of the present invention is not limited thereby.

The effect of the present invention is believed to be provided by the following mechanism. Namely, it is believed that, since a peptide having a predetermined length with thiolactone structure, which is represented by Formula (1), functions as an antagonist for VirS that is a sensor for extracellular signal, expression of a toxin gene which is regulated at downstream of VirR/VirS system is suppressed. It is also believed that, since a peptide having a predetermined length with substituted or non-substituted lactam structure, which is represented by Formula (2), functions as an antagonist for VirS that is a sensor for extracellular signal, expression of a toxin gene regulated at downstream of VirR/VirS is suppressed. It is also considered that the three-dimensional structure related to the position of an aromatic amino acid in the aforementioned peptide sequence (in particular, $X^2$ in the peptide represented by Formula (1) and $X^6$ in the peptide represented by Formula (2)) exhibits an influence on the binding activity for VirS. It is also believed that, as an exceptional case, the reason for not having the aforementioned preservative replacement when $X^2$ or $X^6$ is Phe may be also related to the binding activity for VirS. However, this mechanism is just assumption, and the technical scope of the present invention is not limited thereby.

The peptide represented by Formula (1) or Formula (2) can be produced by a skilled person in the art according to any method. For example, the peptide can be obtained by cyclization of a linear peptide synthesized by a solid phase synthesis method or expressed in a host cell. The peptide represented by Formula (1) or Formula (2) may be also a peptide that has been purified/isolated by a conventionally known method from a cultured broth of *Clostridium butyricum*.

For a case where the peptide is synthesized by a solid phase synthesis method, a method known to a skilled person in the art such as Fmoc (9-fluorenylmethyloxycarbonyl) synthetic method, benzyloxycarbonyl method, and Boc (t-butyloxycarbonyl) synthetic method can be used, although it is not particularly limited thereto. If descriptions are given by having the Fmoc synthetic method as an example, from Fmoc-amino acid bound to a solid phase such as a resin (for example, Wang resin or 2-chlorotriethylchloride resin), Fmoc group as a protecting group is removed by using a base such as 20% (v/v)piperidine/N,N'-dimethylformamide (DMF). Then, by repeating operations of reacting following Fmoc-amino acids, a peptide with desired sequence can be synthesized. According to a coloration reaction such as Kaiser Test, the deprotection reaction can be confirmed. For the separation of the peptide from the resin or removal reaction including deprotection of side chain-protecting group, a treatment with acid (for example, trifluoroacetic acid (TFA)) or alkali (for example, piperidine) can be carried out. When the deprotection is carried out by an alkali treatment, a peptide having thiolactone structure represented by Formula (1) can be preferentially obtained if short treatment time is applied (for example, about 3 minutes), and a peptide having lactam structure represented by Formula (2) can be preferentially obtained if long treatment time is applied (for example, 15 minutes to 1 hour). Alternatively, the peptide having lactam structure represented by Formula (2) can be also obtained by an alkali conversion treatment of the peptide with thiolactone structure represented by Formula (1) by using ammonia or the like.

When the peptide is prepared by expressing it in a host cell, a vector in which a polynucleotide encoding a desired peptide sequence (for example, Cys-Phe-Trp-Ala-His (SEQ ID NO: 1)) is integrated into the downstream of a promoter is introduced to a host cell. Examples of the vector include plasmid, cosmid, virus, phage, or the like. The promoter can be suitably selected depending on a host cell, and examples thereof include T7 promoter, lac promoter, trp promoter, tac promoter, spa promoter, SV40 promoter, CMV promoter, EF promoter, or the like. Examples of the host cell include prokaryotic cells such as *E. coli* or *Bacillus subtilus*; yeast; mold; mammalian cells such as HEK-293 cell, COS-7 cell, or CHO cell; insect cells with baculovirus; and species such as silkworm. As for the method for introduction into a host cell, a method well known to a skilled person in the art such as microinjection, calcium phosphate method, electroporation, or transfection using liposome can be employed. The peptide synthesized by a host cell can be purified by any method such as dialysis, column processing, or washing and recovered.

The linear peptide obtained by the above method can be cyclized by a reaction using coupling reagent such as PyBOP (hexafluorophosphoric acid (benzotriazol-1-yloxy) tripyroolidinophosphonium) or DCC (N,N'-dicyclohexyl-carbodiimide). For example, the peptide may be dissolved in N,N'-dimethylacetamide (DMA) or the like such that the peptide concentration is about 0.5 to 2 mg/ml and reacted for 1 to 20 hours after adding about 1 to 5 equivalents of PyBOP and dimethylaminopyridine. The coupling reaction may be performed at room temperature or under heating at about 20 to 50° C. It may be also performed in an inert gas atmosphere such as N2.

The cyclic peptide obtained by the above method can be purified/isolated by a method well known to a skilled person in the art, for example, solid phase extraction (for example, Sep-Pac (registered trademark) manufactured by Waters Corporation can be used) or liquid chromatography (for example, reverse phase HPLC). Furthermore, the structure of a synthesized cyclic peptide can be determined by a method well known to a skilled person in the art, for example, MS (for example, ESI-MS) or $^1$H NMR.

[Toxin Production Inhibitor]

The second aspect of the present invention is to provide a toxin production inhibitor for a bacterium belonging to the genus *Clostridium*, which contains the peptide of Formula (1) as an effective ingredient. According to other embodiment of the present invention, a use of the peptide of Formula (1) for inhibiting the toxin production by a bacterium belonging to the genus *Clostridium* is provided.

According to other embodiment of the present invention, a toxin production inhibitor for a bacterium belonging to the genus *Clostridium*, which contains the peptide of Formula (2) as an effective ingredient, is provided. According to other embodiment of the present invention, a use of the peptide of Formula (2) for inhibiting the toxin production by a bacterium belonging to the genus *Clostridium* is provided.

The bacterium belonging to the genus *Clostridium* is a bacterium that causes health damages such as gas gangrene, colitis, necrotic enteritis of livestock or poultry, diarrhea, enterotoxemia, cellulitis, uterine infection, bacteremia, food poisoning, or tetanus.

In the present invention, the bacterium belonging to the genus *Clostridium* means a bacterium of the genus *Clostridium* except *Clostridium butyricum*, and examples thereof include *Clostridium welchii* (*Clostridium perfringens*), *Clostridium difficile* (*Clostridium difficile*), botulinus (*Clostridium botulinum*), tetanus bacillus (*Clostridium tetani*), and *Clostridium novyi* (*Clostridium novyi*). It is preferably selected from the group consisting of *Clostridium welchii* (*Clostridium perfringens*), *Clostridium difficile* (*Clostridium difficile*), and botulinus (*Clostridium botulinum*). The present invention is particularly preferably applied to *Clostridium welchii* (*Clostridium perfringens*).

Toxins produced by a bacterium belonging to the genus *Clostridium* are, although not particularly limited thereto, a toxin that can be regulated at downstream of VirR/VirS system, for example. More specific examples thereof include alpha-toxin (phospholipase C), theta-toxin (hemolysin), kappa-toxin (collagenase), toxin regulated by VirR regulated RNA (VR-RNA), α-clostripain, collagen adhesin, beta 2-toxin, hemolytic toxin, mu-toxin (hyaluronidase), enterotoxin, sialidase, delta-toxin (hemolysin), nu-toxin (DNase), neuraminidase, and the like.

According to the present invention, the aforementioned health damages caused by a bacterium belonging to the genus *Clostridium* can be prevented, treated, and/or controlled.

The toxin production inhibitor of the present invention contains the peptide represented by Formula (1) in an amount that is sufficient for exhibiting a desired effect (effective amount). Alternatively, the toxin production inhibitor of the present invention contains the peptide represented by Formula (2) in an amount that is sufficient for exhibiting a desired effect (effective amount). Although the toxin production inhibitor may consist of the peptide represented by Formula (1) or the peptide represented by Formula (2), preferably, the toxin production inhibitor is prepared by a common method as an oral or parenteral preparation by using in combination an additive acceptable for preparation. Examples of the additive acceptable for preparation include a vehicle, a stabilizer, a preservative, a wetting agent, an emulsifier, a lubricant, a sweetener, a colorant, a flavor, a buffering agent, an anti-oxidant, a pH controlling agent, a binder, a thickening agent, a dispersing agent, a suspending agent, a disintegrant, an anti-bacterial agent, a surfactant, and the like. The dosage form is not particularly limited, and it can be suitably determined. Examples thereof include a tablet, a powder, a fine granule, a granule, a capsule, a pill, a sustained-release preparation, a solution, a suspension, an emulsion, a lotion, an injection solution, a drop solution, an external preparation, a suppository, a patch, and the like.

During the storage period, the peptide represented by Formula (1) may naturally undergo a conversion reaction to have a structural change into the peptide represented by Formula (2). Furthermore, when the peptide represented by Formula (2) is synthesized by using the peptide represented by Formula (1) as a raw material, the peptide represented by Formula (2) may contain a small amount of the peptide represented by Formula (1) even after purification. Thus, with regard to the toxin production inhibitor, "the peptide represented by Formula (1)" may contain the peptide represented by Formula (2) at an impurity level or "the peptide represented by Formula (2)" may contain the peptide represented by Formula (1) at an impurity level. Furthermore, the toxin production inhibitor may contain the peptide represented by Formula (1) and the peptide represented by Formula (2) at any ratio. In that case, the ratio between the peptide represented by Formula (1) and the peptide represented by Formula (2) is 1:1000 to 1000:1 (weight ratio), for example, although it is not particularly limited thereto.

According to the third aspect of the present invention, a toxin production inhibitor for a bacterium belonging to the genus *Clostridium* containing, as an effective ingredient, a cultured broth of *Clostridium butyricum* or a dried product of the broth is provided. According to other embodiment of the present invention, a use of cultured broth of *Clostridium butyricum* or a dried product of the broth for inhibiting toxin production by a bacterium belonging to the genus *Clostridium* is provided.

An autoinducer peptide produced by a bacterium is generally secreted extracellularly. AgrD (SEQ ID NO: 2) secreted by *Staphylococcus aureus* is believed to have a structure that is represented by the following Formula (3).

[Chem. 5]

$$NH_2\text{-Tyr-Ser-Thr}-Cys-Asp$$

(with a cyclic structure involving S, Cys, Asp, Phe, Ile, Met, and O=C)

(3)

Meanwhile, *Clostridium butyricum* MIYAIRI 588 has a gene encoding the autoinducer peptide AgrD with the following sequence, which may be a homolog of AgrD of *Staphylococcus aureus*.

Chem. 6

Comparison of AgrD sequence

| | | |
|---|---|---|
| S. a | MNTLFNLFFDFITGILKNIGNIAAYS | |
| C. p SM101 | MKKLNKNLLTLFAALTTVVATTVATS | |
| C. b MIYAIRI 588 | MKTKILMGIATVATVMASIVSTS | |
| S. a | TCDFIM DEVEVPKELTQLHE | SEQ ID NO: 2 |
| C. p SM101 | ACLWFT HQPEEPKSLRDE | SEQ ID NO: 3 |
| C. b MIYAIRI 588 | <u>ACFWAH</u> YQPEEPKSLREE | SEQ ID NO: 4 |

(S. a: *Staphylococcus aureus*, C. p: *Clostridium perfringens*, C. b: *Clostridium butyricum*)
(The sequence with underline corresponds to the peptide according to the present invention).

In AgrD contained in *Clostridium butyricum* miyairi 588, a sequence corresponding to the peptide represented by Formula (1) or Formula (2) is included. Although the technical scope of the present invention is not limited, the inhibitory activity of broth of *Clostridium butyricum* on toxin production by a bacterium belonging to the genus

*Clostridium* such as *Clostridium welchii* is believed to be based on the following mechanism. Specifically, it is believed that, as the broth of *Clostridium butyricum* contains AgrD as a peptide represented by Formula (1) or Formula (2), the inhibitory activity on toxin production by a bacterium belonging to the genus *Clostridium* such as *Clostridium welchii* is exhibited. However, this mechanism is just assumption, and the technical scope of the present invention is never limited.

*Clostridium butyricum* is a spore-forming and anaerobic gram positive *bacillus* which repeats division and proliferation as long as a balance in nutrition is maintained (feed cells), but it forms spores in bacterial body when the balance is disrupted. Without being limited to anaerobic bacteria, many bacteria, when in the form of feed cells, are readily killed if they are kept in a dry state. However, since the spores are resting cells, they have strong resistance to various outer environments such as dryness, heat, and chemical agents, and thus have a good storing property.

Furthermore, as described above, *Clostridium butyricum* has a spore-forming property and resistance to various outer environments when it is in a spore state. Therefore, when *Clostridium butyricum* is orally administered in spore form to a human or an animal, it is not completely killed even under contact with digestive juice such as gastric acid, intestine juice or bile acid, so that it can be delivered to a fermentation area ranging from a lower section of small intestine to large intestine and can proliferate.

Furthermore, *Clostridium butyricum* is widely available as a commercial product including probiotics, feed additives, or food products, and as no side effect is observed even when it is administered for a long period of time to a mammal such as human and livestock, high safety has been confirmed therefor.

Examples of *Clostridium butyricum* (*Clostridium butyricum*) which can be used in the present invention include *Clostridium butyricum* miyairi, *Clostridium butyricum* (FERM P-11868), *Clostridium butyricum* (FERM P-11868), *Clostridium butyricum* (FERM P-11869), *Clostridium butyricum* (FERM P-11870), *Clostridium butyricum* Prazmowski 1880 (NBRC 13949), *Clostridium butyricum* Prazmowski 1880 (NBRC 3315), *Clostridium butyricum* Prazmowski 1880 (NBRC 3858), *Clostridium butyricum* ATCC859 (*Clostridium butyricum* ATCC 859), *Clostridium butyricum* ATCC860 (*Clostridium butyricum* ATCC 860), *Clostridium butyricum* ATCC3627 (*Clostridium butyricum* ATCC 3627), and *Clostridium butyricum* ATCC19398 (*Clostridium butyricum* ATCC 19398). Preferably, *Clostridium butyricum* (*Clostridium butyricum*) is one or more types selected from the group consisting of *Clostridium butyricum* miyairi 588 (*Clostridium butyricum* MIYAIRI 588, FERM BP-2789), *Clostridium butyricum* miyairi 585 (FERM BP-06815), *Clostridium butyricum* miyairi 595 (FERM BP-06816), and *Clostridium butyricum* miyairi 630 (FERM BP-06817). More preferably, it is *Clostridium butyricum* miyairi 588 (*Clostridium butyricum* MIYAIRI 588, FERM BP-2789). Meanwhile, *Clostridium butyricum* miyairi 588 strain was deposited as FERM BP-2789 with National Institute of Microbial Technology, Agency of Industrial Science and Technology on May 1, 1981 (presently, National Institute of Technology and Evaluation, Patent Microorganism Depositary) (zip code 292-0818, Kazusakamatari, 2-5-8, Kisarazu-shi, Chiba, Japan). On Mar. 6, 1990, it was transferred to an international depository organization based on Budapest Treaty, and has been deposited with deposit number of FERM BP-2789.

The toxin production inhibitor according to the third embodiment of the present invention contains, as an effective ingredient, a cultured broth of *Clostridium butyricum* or a dried product of the broth.

*Clostridium butyricum* miyairi is commercially provided byMIYARISAN PHARMACEUTICAL CO., LTD. as probiotics. Because it does not exhibit any side effect when administered for a long period of time to a human or an animal, it is particularly preferable for a use in the present invention. Meanwhile, *Clostridium butyricum* as an effective ingredient may be used either singly or in combination of two or more types.

In the present invention, the culture product of *Clostridium butyricum*, i.e., "cultured broth of *Clostridium butyricum* or a dried product of the broth" is obtained by a known method for culturing microorganisms, for example, by a method described in JP-A No. 08-252088. One embodiment thereof is described hereinbelow: *Clostridium butyricum* is seeded to a medium consisting of 1.0 (w/v) % peptone, 1.0 (w/v) % yeast extract, 1.0 (w/v) % corn starch, and 0.2 (w/v) % precipitated calcium carbonate at $10^5$ to $10^6$ cells/mL, and the "broth of *Clostridium butyricum*" is obtained by static culture for 48 hours at 37° C. In order to obtain the "dried product of a broth", the obtained broth is subjected to a drying treatment by air drying or the like at 0 to 80° C., and preferably 10 to 20° C., for 1 to 24 hours, and preferably 5 to 18 hours. Alternatively, a drying treatment under reduced pressure at 0 to 80° C., and preferably 10 to 20° C. and 0.05 to 500 Torr (7 Pa to 66.7 kPa), and preferably 1 to 100 Torr (133 Pa to 13.3 kPa), for 1 to 24 hours, and preferably 2 to 15 hours can be carried out. Spray dry, freeze dry, or the like may be employed for obtaining a dried product.

The medium used for culturing *Clostridium butyricum* of the present invention may vary depending on the type of a strain for use. Further, the medium may be any of a synthetic medium or a natural medium as long as it contains a carbon source, a suitable amount of nitrogen source, and other nutrients including inorganic salts and vitamins that can be utilized by *Clostridium butyricum*.

Examples of the carbon source used in the medium of the present invention are not particularly limited as long as it is a carbon source that can be utilized by a strain to be used. As for the carbon source, although it is not particularly limited to a sugar, a sugar or a sugar containing material usable by a microbe to be used is preferably used considering the proliferation of microbial body. Specific examples of the carbon source that may be used include, considering the utilization property, cellobiose, glucose, fructose, galactose, lactose, maltose, mannose, melibiose, raffinose, salicin, starch, sucrose, trehalose, xylose, dextrin, soluble starch, and molasses. Among those carbon sources, starch, glucose, fructose, sucrose, and molasses are preferably used. Considering *Clostridium butyricum* to be used, the carbon source may be used either singly or in combination of two or more types. Concentration of the carbon source to be added may vary depending on the type of *Clostridium butyricum* for use, type of the carbon source, medium composition of the medium for use excluding the carbon source, or the like. However, it is generally 0.5 to 5 (w/v) %, and preferably 2 to 4 (w/v) %.

Furthermore, examples of the nitrogen source and vitamins include meat extract, peptone, soybean peptone, protease peptone, yeast extract, liver extract, digested serum powder, hydrolysate of soybean or wheat, soybean powder, milk casein, casamino acid, various amino acids, corn steep liquor, organic nitrogen compounds such as hydrolysate of an animal, a plant, or a microorganism, and ammonia salt such as ammonium sulfate. Among those nitrogen source, peptone, soybean peptone, protease peptone, yeast extract, digested serum powder, meat extract, liver extract, corn steep liquor, and hydrolysate of soybean or wheat are preferably used. To improve the growth of *Clostridium butyricum* to be used, one or more types of the nitrogen source or vitamins may be selected and used. Concentration of the nitrogen source for addition may vary depending on the type of a bacterial strain for use or nitrogen source, or medium composition of a medium excluding nitrogen source. However, when peptone containing a large amount of nitrogen source is used, it is generally 0.5 to 4 (w/v) %, and preferably 1 to 3 (w/v) %. When a seasoning solution or corn steep liquor containing a large amount of nitrogen source and vitamins is used, it is generally 0.5 to 5 (w/v) %, and preferably 1 to 4 (w/v) %. When yeast extract or meat extract containing a large amount of vitamins is used, it is generally 0.5 to 4 (w/v) %, and preferably 1 to 3 (w/v) %.

Furthermore, as for the inorganic salt, one or more types selected from, such as phosphate, hydrochloride, sulfate, butyrate, propionate, halide such as chloride, and acetate of magnesium, manganese, calcium, sodium, potassium, molybdenum, strontium, boron, copper, iron, tin, and zinc can be used. It is also possible to add, if necessary, a agent such as an anti-foaming agent, vegetable oil, a surfactant, blood, a blood component, and an antibiotic material, a physiologically active material such as plant or animal hormone, or a reducing agent such as thioglycolate and cysteine suitably to the medium.

Conditions for culture to be performed in the present invention may vary depending on a physiological property such as growth range (such as pH, and temperature) of *Clostridium butyricum* used for the present invention. However, because *Clostridium butyricum* is an obligate anaerobic microbe, it is necessary to be cultured without any aeration or under anaerobic conditions by supplying nitrogen or carbonic acid gas, or by adding a reducing agent to a medium and lowering the oxidation and reduction potential. Culture conditions for such case are appropriately selected according to the growth range of microbial strain to be used, medium composition, or method for culture, but it is not particularly limited as long as the subject strain can proliferate. Specifically, the culture temperature is 20 to 42° C. in general, and preferably 35 to 40° C.

Furthermore, according to the present invention, proliferation of *Clostridium butyricum* is promoted when an acid generated during the culture is neutralized with an alkali, and thus calcium carbonate may be added in advance to the medium. In that case, the added amount of calcium carbonate is generally 0.1 to 4 (w/v) %, and preferably 0.2 to 2.5 (w/v) %. Alternatively, the neutralization step may be performed while pH of the medium is suppressed to a pre-set pH range by using an aqueous alkali solution of sodium hydroxide, sodium hydrogen carbonate, sodium carbonate, potassium hydroxide, and potassium carbonate. Meanwhile, when an aqueous alkali solution is used, the "pre-set pH" indicates a pH that has been set in advance during the culture period, and "pre-set pH range" indicates a pH range which is allowed during the culture period, and it is generally represented as pre-set pH±allowable difference. According to the present invention, the pre-set pH is generally set within the range of from 5.0 to 7.5, and preferably within the range of from 5.5 to 6.5. The pre-set pH range is pre-set pH±0.5, and preferably pre-set pH±0.2.

Meanwhile, in the present invention, pH of the medium during culture is in near-neutral region, and preferably 6.5 to 7.5 when bacteria are inoculated. Meanwhile, when an aqueous alkali solution is used, it is preferable to maintain it within a pre-set pH range under gentle stirring so as not to incorporate any oxygen. By controlling pH at the time of inoculation and proliferation of bacteria, the bacterial cell density can be dramatically increased.

According to the culture performed in the present invention, the initial culture concentration of *Clostridium butyricum* is not particularly limited if it is within a region in which *Clostridium butyricum* can grow. In general, it is the same as the concentration employed for culture of *Clostridium butyricum*. Specifically, it is generally $10^4$ to $10^7$ cells/mL, and preferably $10^5$ to $10^6$ cells/mL.

Preferably, the broth of *Clostridium butyricum* is a broth after middle phase of exponential growth. As described herein, the term "middle phase of exponential growth" indicates an approximately middle period between the start of growth and the arrival at the stationary phase. For example, it indicates a period in which OD at wavelength of 660 nm is between 0.5 and 1.0. The broth of *Clostridium butyricum* after middle phase of exponential growth, which is preferably used in the present invention, is not particularly limited as long as the inhibitory activity on toxin production by *Clostridium welchii* is exhibited. For example, it is a solution recovered within 500 hours from the start of culture. More preferably, it is a solution recovered within 100 hours from the start of culture.

As for the toxin production inhibitor of the present invention, the broth or a dried product of the broth may be used as an effective ingredient. Further, the broth may be centrifuged before drying, and a precipitate, a supernatant, or a dried product thereof containing bacteria (bacterial cell body or spore) obtainable by centrifuge or the like can be also used as an effective ingredient. Thus, according to one embodiment of the present invention, a toxin production inhibitor that contains, as an effective ingredient, a precipitate or a supernatant containing bacteria (bacterial cell body and/or spore) which is obtainable by centrifuge of a cultured broth of *Clostridium butyricum*, or a dried product of the precipitate or supernatant is provided.

When *Clostridium butyricum* is orally administered, it reaches lower small intestine or large intestine and proliferates therein as described above. Thus, by orally administering a precipitate containing the bacteria (bacterial cell body or spore) which is obtainable by centrifuge or the like, it is expected to have a probiotic effect. Meanwhile, because AgrD secreted by a bacterium belonging to the genus *Clostridium* is water soluble, it is possible that a supernatant obtainable by centrifuge or the like is recovered and a supernatant fraction containing secreted AgrD is obtained and used for such as an injection solution and an ointment.

Conditions for centrifuge are not particularly limited, but they are 10 to 30 minutes at 2,000 to 6,000 g for example. As for the method for drying a precipitate or a supernatant containing bacteria (bacterial cell body or spore), reference can be suitably made to the method for obtaining "dried product of broth" described above.

From the broth obtained as described above, or precipitate or supernatant obtained by further centrifuge of the broth, the peptide according to the present invention may be additionally concentrated/purified by using a method that is well known to a skilled person in the art. Method for concentration is not particularly limited. By using a method well known to a skilled person in the art such as dialysis, ultra filtration, and liquid chromatography, a fraction having high activity can be recovered while confirming the toxin production inhibitory effect by using a means described in Examples. In the broth according to the present invention, or precipitate or supernatant obtained by further centrifuge of the broth, the aforementioned concentrate or purified product is also included.

With regard to the bacteria belonging to the genus *Clostridium* or toxins produced by the bacteria belonging to the genus *Clostridium* of this embodiment, reference can be made to the descriptions given above regarding the toxin production inhibitor containing the peptide of the present invention.

The toxin production inhibitor of the present invention contains a cultured broth of *Clostridium butyricum* or a dried product of the broth in an amount sufficient for exhibiting the desired effect (effective amount). According to other embodiment of the present invention, the toxin production inhibitor of the present invention contains a precipitate or a supernatant which contains the bacteria obtainable by centrifuge of the cultured broth of *Clostridium butyricum* or a dried product of the precipitate or supernatant in an amount sufficient for exhibiting the desired effect (effective amount). The toxin production inhibitor may consist of the broth or a dried product thereof, or a supernatant or precipitate of the broth or a dried product thereof. However, by using a common method, it is preferably prepared as an oral preparation or a parenteral preparation using in combination an additive allowed for preparation.

As for the additive allowed for preparation, reference can be made to the descriptions given above regarding the toxin production inhibitor containing the peptide of the present invention.

[Method for Preventing and/or Treating Health Damages Caused by Bacteria Belonging to Genus *Clostridium*]

According to one embodiment of the present invention, a method for preventing and/or treating health damages caused by a bacterium belonging to genus *Clostridium*, including administering an effective amount of the peptide represented by Formula (1) to a patient is provided. According to other embodiment of the present invention, a method for preventing and/or treating health damages caused by a bacterium belonging to genus *Clostridium*, including administering an effective amount of the peptide represented by Formula (2) to a patient is provided.

According to other embodiment of the present invention, a method for preventing and/or treating health damages caused by a bacterium belonging to genus *Clostridium*, including administering an effective amount of a cultured broth of *Clostridium butyricum* or a dried product of the broth to a patient is provided. According to other embodiment of the present invention, a method for preventing and/or treating health damages caused by a bacterium belonging to genus *Clostridium*, including administering an effective amount of a precipitate or a supernatant which contains the bacteria (bacterial cell body and/or spores) obtainable by centrifuge of a cultured broth of *Clostridium butyricum* or a dried product of the precipitate or supernatant to a patient is provided.

As described herein, the term "effective amount" indicates an amount of an effective ingredient that is at least necessary for exhibiting a desired effect such as prevention and/or treatment of health damages caused by a bacterium belonging to the genus *Clostridium*. Furthermore, the "patient" indicates, although it is not particularly limited, a human; a pet such as dog and cat; a laboratory animal such as mouse and rat; poultry such as chicken, quail, turkey, duck, and goose; livestock such as pig, cow, horse, sheep, and goat; and a fish.

The descriptions given above for the toxin production inhibitor are also applied, with suitable modifications, to this embodiment.

[Pharmaceutical Composition]

The fourth aspect of the present invention is to provide a pharmaceutical composition which contains a toxin production inhibitor containing, as an effective ingredient, the peptide represented by Formula (1), or the cultured broth of *Clostridium butyricum* or a dried product of the broth. According to other embodiment of the present invention, a pharmaceutical composition which contains a toxin production inhibitor containing, as an effective ingredient, the peptide represented by Formula (2), or the cultured broth of *Clostridium butyricum* or a dried product of the broth is provided. According to one embodiment of the present invention, a pharmaceutical composition which contains a toxin production inhibitor containing, as an effective ingredient, a precipitate or a supernatant which contains the bacteria (bacterial cell body and/or spores) obtainable by centrifuge of cultured broth of *Clostridium butyricum* or a dried product of the precipitate or supernatant is provided.

The pharmaceutical composition may be administered according to any administration route considered to be appropriate by a skilled person in the art. For example, the pharmaceutical composition may be administered orally, intravenously, intramuscularly, intrathecally, intraperitoneally, transdermally (for example, as an ointment), or by an inhaling administration. The pharmaceutical composition of the present invention contains a pharmaceutically acceptable carrier depending on each of those administration routes. The pharmaceutically acceptable carrier is not particularly limited, but examples thereof include an excipient such as lactose or starch; a binder such as dextrin or cellulose; a solvent such as water or an organic solvent; and a base preparation such as Vaseline, bee wax, or paraffin.

The blending ratio of effective ingredients in the pharmaceutical composition is, although not particularly limited, as follows; the toxin production inhibitor is 0.001 to 50% by weight relative to the whole pharmaceutical composition, for example.

Furthermore, the pharmaceutical composition of the present invention may optionally contain, in addition to the above effective ingredients, antibiotics, vitamins (for example, vitamin C and vitamin E), amino acids, peptides, minerals (for example, zinc, iron, copper, manganese, and the like), nucleic acids, polysaccharides, fatty acids, and galenical pharmaceuticals. Examples of the antibiotics include, although not particularly limited, a penicillin-based antibiotics such as penicillin or ampicillin, a cephem-based antibiotics such as cephamycin, a glycopeptide-based antibiotics such as vancomycin, a carbapenem-based antibiotics such as meropenem, a chloramphenicol-based antibiotics, a tetracycline-based antibiotics such as tetracycline or doxycyclin, and a macrolide-based antibiotics such as erythromycin.

Dosage of the pharmaceutical composition of the present invention can be appropriately varied according to a symptom or conditions to be treated, age, or the like. For example, it is 0.1 to 1000 mg/kg of body weight in terms of effective ingredient.

The pharmaceutical composition of the present invention may be administered to any one of human and non-human animals.

[Food Product]

The fifth aspect of the present invention is to provide a food product which contains a toxin production inhibitor containing, as an effective ingredient, the peptide represented by Formula (1), or the cultured broth of *Clostridium butyricum* or a dried product of the broth. According to other embodiment of the present invention, a food product which contains a toxin production inhibitor containing, as an effective ingredient, the peptide represented by Formula (2), or the cultured broth of *Clostridium butyricum* or a dried product of the broth is provided. According to one embodiment of the present invention, a food product which contains a toxin production inhibitor containing, as an effective ingredient, a precipitate or a supernatant which contains the bacteria (bacterial cell body and/or spores) obtainable by centrifuge of a cultured broth of *Clostridium butyricum* or a dried product of the precipitate or supernatant is provided.

The food product containing the toxin production inhibitor of the present invention can inhibit the toxin production by a bacterium belonging to the genus *Clostridium* not only in a living body after intake of the food product but also in a food product before the intake. Because the bacterium belonging to the genus *Clostridium* forms a heat-resistant spore, it is not easily sterilized even by heating. Thus, the present invention is advantageous in that the toxin production by a bacterium belonging to the genus *Clostridium* can be inhibited even in a food product which is difficult to be sterilized by heating or not sufficiently sterilized by heating.

As described herein, the "food product" indicates a product other than pharmaceuticals, and it is not particularly limited as long as it has form which can be orally administered to a mammal. Shape of the product can be any one of liquid product (solution, suspension, or emulsion), semi-solid liquid product, powder, and solid-molded product. As such, the food product may have drink form or tablet form of nutrition aid food product such as supplement.

Specific examples of the food product include instant food products such as instant noodle, retort food product, canned food, microwave food product, instant soup/miso soup product, or freeze-dry food product; beverages such as soft drink, fruit juice drink, vegetable beverage, soymilk drink, coffee beverage, tea drink, powdered drink, concentrate drink, nutritional drink, or alcohol; wheat flour product such as bread, pasta, noodle, cake mix, powder for deep-fried food, or bread powder; confectioneries such as candy, caramel, chewing gum, chocolate, cookie, biscuit, cake, pie, snack, cracker, Japanese snack, or dessert snack; seasonings such as sauce, seasoning of processed tomato, flavor seasoning, cooking mix, sauces, dressings, clear soup, and curry or stew stocks; oils and fats such as processed oils and fats, butter, margarine, or mayonnaise; dairy products such as milk beverage, yoghurt, *lactobacillus* beverage, ice cream, or cream; processed sea products such a fish meat ham/sausage or kneaded sea product; processed livestock product such as ham or sausage of livestock meat; processed agricultural product such as canned agricultural product, jam/marmalade, pickles, cooked beans, or cereal; frozen food products; and nutritional food products.

The food product according to the present invention can be preferably used for a person who suffers from health damages that are caused by a bacterium belonging to the genus *Clostridium* or a person at high risk of having such damage. Herein, with regard to the person at high risk of having such damage, a person who is found to have a high risk after considering various indices including body composition or diet habit or by diagnosis/determination such as health diagnosis, and a person recognized to have high risk by himself or other person are included, for example.

The "food product" of the present invention also includes a health food product, a functional food product, a food for specified health use, a nutritional supplementary food product, a food product with reduced disease risk label, and a food product categorized as a food product for patient.

The food product of the present invention may be added with, in addition to the aforementioned effective ingredient, an ingredient having other activities. Furthermore, by blending a daily consumed food product, a health food product, a functional food product, or a supplement (for example, a food product containing one or more kinds of minerals such as calcium or magnesium and vitamins such as vitamin K) with the effective ingredient of the present invention, a food product having the activities based on other components in addition to the effect of the present invention can be also provided.

Blending ratio of the effective ingredient in food product is not particularly limited. For example, the toxin production inhibitor is 0.001 to 50% by weight relative to dry weight of a food product.

[Animal Feed]

The sixth aspect of the present invention is to provide an animal feed which contains a toxin production inhibitor containing, as an effective ingredient, the peptide represented by Formula (1), or the cultured broth of *Clostridium butyricum* or a dried product of the broth. According to other embodiment of the present invention, an animal feed which contains a toxin production inhibitor containing, as an effective ingredient, the peptide represented by Formula (2), or the cultured broth of *Clostridium butyricum* or a dried product of the broth is provided. According to one embodiment of the present invention, an animal feed which contains a toxin production inhibitor containing, as an effective ingredient, a precipitate or a supernatant which contains the bacteria (bacterial cell body and/or spores) obtainable by centrifuge of a cultured broth of *Clostridium butyricum* or a dried product of the precipitate or supernatant is provided.

The animal feed of the present invention is given to a non-human animal including a pet such as dog and cat; a laboratory animal such as mouse and rat; poultry such as chicken, quail, turkey, duck, goose, a hybrid between mallard and duck, and pheasant; livestock such as pig, cow, horse, sheep, and goat; and a fish and a shell fish such as salmon, sweet fish, tuna, yellowtail, flounder, seabream, eel, and shrimp, but it is not limited thereto.

As health damages caused by a bacterium belonging to the genus *Clostridium*, *Clostridium welchii* infection in poultry such as chicken can be especially mentioned. Damages caused by *Clostridium welchii* infection are significant in a broiler production, and the mortality rate is sometimes as high as 50%. In this regard, by feeding the animal feed containing the toxin production inhibitor of the present invention, it is expected that *Clostridium welchii* infection in poultry is effectively prevented, inhibited, and/or treated.

Raw material of the animal feed of the present invention is not particularly limited, and examples thereof include corn, sorghum, barley, wheat, rice, wheat flour, rice flour, soybean flour, rice bran, soymeal, safflower meal, wheat bran, corn gluten meal, corn gluten feed, powdered skim milk, fish meal, starch, cellulose, vitamins, beer yeast, calcium carbonate, and calcium phosphate. Shape of the animal feed is not particularly limited either, and it can be arbitrarily selected, such as a pellet, powder feed, solid feed, liquid feed, and silage to which the above toxin production inhibitor is added, for example. The blending ratio of the effective ingredient in the animal feed is not particularly limited. For example, the toxin production inhibitor is 0.01 to 10% by weight relative to dry feed weight.

EMBODIMENTS (1) A peptide represented by the following Formula (1):

[Chem. 7]

$$R^1-NH-\underset{S}{\overset{}{\text{Cys}}}-X^1\quad X^2\quad X^3\quad X^4$$
(1)

in Formula (1), $R^1$ is selected from the group consisting of a hydrogen atom, an amino acid and a derivative thereof, and, with or without substituent(s), an acyl group having to 10 carbon atoms, a benzyloxycarbonyl group, a 9-fluorenylmethyloxycarbonyl group, and a phenylisothiocyanate group, $X^1$ and $X^2$ are each independently selected from the group consisting of Ala, Gly, Trp, Met, Pro, Phe, Val, Leu, Ile, and Tyr, and $X^3$ and $X^4$ are any amino acid, with the proviso that, when $X^2$ is Phe, $X^4$ is Thr, when $X^4$ is Ala, $X^1$ is Ala, and when $X^4$ is Thr, $X^3$ is Trp or Ala.

(2) The peptide according to (1), wherein $X^2$ in Formula (1) is selected from the group consisting of Phe, Trp, and Tyr.

(3) The peptide according to (1) or (2), wherein $X^4$ in Formula (1) is selected from the group consisting of His, Ala, Thr, and Ser.

(4) The peptide according to any one of (1) to (3), wherein $R^1$ in Formula (1) is a hydrogen atom or a benzyloxycarbonyl group.

(5) The peptide according to any one of (1) to (4), wherein $X^3$ in Formula (1) is selected from the group consisting of Ala, Gly, Trp, Met, Pro, Phe, Val, Leu, and Ile.

(6) The peptide according to any one of (1) to (5), wherein $X^1$ in Formula (1) is selected from the group consisting of Phe, Trp, Tyr, Ala, Val, Leu, and Ile.

(7) A peptide represented by the following Formula (2):

[Chem. 8]

$$R^2-N\underset{O}{\overset{Z-X^5}{\underset{X^8}{\overset{}{\text{}}}}}X^6\quad X^7$$
(2)

in Formula (2), $R^2$ is selected from the group consisting of a hydrogen atom, an amino acid and a derivative thereof, and, with or without substituent(s), an acyl group having 1 to 10 carbon atoms, a benzyloxycarbonyl group, a 9-fluorenylmethyloxycarbonyl group, and a phenylisothiocyanate group, $X^5$ and $X^6$ are each independently selected from the group consisting of Ala, Gly, Trp, Met, Pro, Phe, Val, Leu, Ile, and Tyr, $X^7$ and $X^8$ are any amino acid, and Z is selected from the group consisting of Cys, Ser, Thr, Tyr, Asn, and Gln, with the proviso that, when $X^6$ is Phe, $X^8$ is Thr, when $X^8$ is Ala, $X^5$ is Ala, and when $X^8$ is Thr, $X^7$ is Trp or Ala.

(8) The peptide according to (7), wherein Z in Formula (2) is Cys.

(9) The peptide according to (7) or (8), wherein $X^6$ in Formula (2) is selected from the group consisting of Phe, Trp, and Tyr.

(10) The peptide according to any one of (7) to (9), wherein $X^8$ in Formula (2) is selected from the group consisting of His, Ala, Thr, and Ser.

(11) The peptide according to any one of (7) to (10), wherein $R^2$ in Formula (2) is a hydrogen atom or a benzyloxycarbonyl group.

(12) The peptide according to any one of (7) to (11), wherein $X^7$ in Formula (2) is selected from the group consisting of Ala, Gly, Trp, Met, Pro, Phe, Val, Leu, and Ile.

(13) The peptide according to any one of (7) to (12), wherein $X^5$ in Formula (2) is selected from the group consisting of Phe, Trp, Tyr, Ala, Val, Leu, and Ile.

(14) A toxin production inhibitor for a bacterium belonging to the genus *Clostridium* including, as an effective ingredient, the peptide according to any one of (1) to (13).

(15) A toxin production inhibitor for a bacterium belonging to the genus *Clostridium* including, as an effective ingredient, a cultured broth of *Clostridium butyricum* (*Clostridium butyricum*) or a dried product of the broth.

(16) The toxin production inhibitor for a bacterium belonging to the genus *Clostridium* according to (15), wherein *Clostridium butyricum* is *Clostridium butyricum* miyairi 588 (*Clostridium butyricum* MIYAIRI 588, FERM BP-2789).

(17) The toxin production inhibitor according to any one of (14) to (16), wherein the bacterium belonging to the genus *Clostridium* is *Clostridium welchii* (*Clostridium perfringens*).

(18) A pharmaceutical composition including the toxin production inhibitor according to any one of (14) to (17).

(19) A food product including the toxin production inhibitor according to any one of (14) to (17).

(20) An animal feed including the toxin production inhibitor according to any one of (14) to (17).

EXAMPLES

The effect of the present invention is explained by using the following examples and comparative examples. However, the technical scope of the present invention is not limited to the following examples. Meanwhile, unless described specifically otherwise, the manipulations were performed at room temperature (25° C.)

Example 1

According to the following method, a peptide (cyclic CFWAH) represented by Formula (1) is synthesized and the inhibitory activity on toxin production by *Clostridium welchii* was confirmed.

[Synthesis of Peptide]

According to the following method, a linear peptide (peptide sequence: Cys-Phe-Trp-Ala-His (SEQ ID NO: 1)) was synthesized. Meanwhile, for Kaiser Test, Kaiser Test kit (manufactured by KOKUSAN CHEMICAL CO., LTD.) was used.

(1) A resin (Fmoc-His (1-Trt)-Wang resin) (manufactured by Novabiochem) in an amount corresponding to 0.3 mmol was weighed and added to a shaker tube for peptide synthesis.
(2) 6 ml of DMF (manufactured by Kanto Chemical Co., Inc.) was added followed by shaking for 60 minutes for swelling the resin.
(3) The resin was washed three times with 6 ml DMF.
(4) The resin was washed with 12 ml of 20% (v/v) piperidine (manufactured by Kanto Chemical Co., Inc.)/DMF.
(5) 6 ml of 20% (v/v) piperidine/DMF was added followed by shaking for 60 minutes.

(6) Kaiser Test was performed.
(7) The resin was washed three times with 6 ml DMF.
(8) Washing with 6 ml of NMP (N-methyl-2-pyrrolidinone, manufactured by Kanto Chemical Co., Inc.) was performed three times.
(9) The following reagents were prepared, each in separate test tube.

| | | |
|---|---|---|
| Fmoc-amino acid | 0.9 mmol/NMP | 3 ml |
| DCC (manufactured by Kanto Chemical Co., Inc.) | 0.9 mmol/NMP | 1.5 ml |
| HOBT•$H_2O$ (HOBT•$H_2O$: 1-hydroxybenzotriazole, manufactured by KOKUSAN CHEMICAL CO., LTD.) | 0.9 mmol/NMP | 1.5 ml |

Meanwhile, as Fmoc-amino acid, Fmoc-Ala-OH, Fmoc-Trp (Boc)-OH, Fmoc-Phe-OH (all manufactured by Novabiochem), and Fmoc-Cys (Trt)-OH (manufactured by KOKUSAN CHEMICAL CO., LTD.) were used in this order. Boc indicates a t-butyloxycarbonyl group and Trt indicates a trityl group.
(10) The above three reagents were added to the shaker tube and shaken for 3 hours or longer.
(11) Kaiser Test was performed to confirm the deprotection reaction.
(12) Washing was performed, three times with 6 ml NMP and three times with 6 ml DMF to wash the resin.
(13) The manipulations from (3) to (12) were repeated four times in total to elongate the peptide.
(14) The resin was washed three times with 6 ml methanol (manufactured by NACALAI TESQUE, INC.).
(15) The obtained peptide bound to resin was dried by using a vacuum dryer.

Meanwhile, with regard to the peptide having 6 to 8 amino acid residues shown in Table 6, synthesis was also performed according to the aforementioned method with appropriately adding Fmoc-amino acid used.

[Removal of Resin and Protecting Group on Side Chain]
with the peptide bound to resin that has been obtained by the above method, a reaction for removing a protecting group on side chain and the resin was performed.
(1) 50 mg of the dried peptide bound to resin was added to a flask, and after adding a cleavage cocktail with the following composition, it was stirred for 60 minutes at room temperature.

TABLE 3

| Composition of cleavage cocktail | |
|---|---|
| TFA (manufactured by Kanto Chemical Co., Inc.) | 860 µl |
| Phenol (manufactured by NACALAI TESQUE, INC.) | 50 µl |
| Ethane dithiol (EDT) (manufactured by Kanto Chemical Co., Inc.) | 30 µl |
| Triisopropylsilane (TIS) (manufactured by Sigma Aldrich) | 10 µl |
| Ultra pure water | 50 µl |

(2) After filtration through a PTFE membrane (φ0.2 µm, manufactured by Kanto Chemical Co., Inc.), 60 ml of cold diethyl ether (manufactured by Kanto Chemical Co., Inc.) was added thereto.
(3) By leaving to stand overnight at 4° C., the peptide was allowed to precipitate.
(4) The precipitated peptide was recovered by sunction filtration using a PTFE membrane (φ4.5 µm, 47 mm, manufactured by ADVANTEC).
(5) The recovered peptide was dissolved in DMSO (500 µl) and purified with Sep-pak (registered trademark) (C18) plus column (manufactured by Waters Corporation) to collect a fraction eluted with 60% (v/v) $CH_3CN$/ultra pure water.
(6) The fraction eluted with 60% (v/v) $CH_3CN$/ultra pure water was concentrated and dried followed by freeze drying to obtain a linear peptide from which the protecting group on a side chain and resin are removed.

[Peptide Cyclization]
The linear peptide that has been obtained by the above method was cyclized as described below to synthesize a peptide having thiolactone structure (cyclic Fmoc-CF-WAH).
(1) 10 mg of the linear peptide was weighed in a flask and added with 4 ml of N,N'-dimethylacetamide (DMA) (manufactured by Kanto Chemical Co., Inc.) to be dissolved.
(2) 20 mg of PyBOP (manufactured by Novabiochem) and 20 mg of dimethylaminopyridine (manufactured by Merck) were added thereto.
(3) After filling with N2 gas, it was stirred for about 10 hours under stirring at room temperature.
(4) The reaction solution was added dropwise to 80 ml of ice cold ultra pure water.
(5) According to purification with Sep-pak (registered trademark) (C18) plus column (manufactured by Waters Corporation), a fraction eluted with 60% (v/v) $CH_3CN$/ultra pure water was collected.
(6) The sample was concentrated and dried followed by freeze drying, and then dissolved in 1 ml of DMSO.
(7) The sample was purified by reverse phase HPLC. Conditions for reverse phase HPLC are as follows.
   Instrument for use: LC-2000 Plus series (manufactured by JASCO Corporation)
   Column: Intertsil ODS-3 20×150 mm (manufactured by GL SCIENCES INC.)
   Flow rate: 10 ml/min
   Detection wavelength: 280 nm

TABLE 4

| Gradient condition | |
|---|---|
| Time (minutes) | $CH_3CN$ (%) |
| 0 | 40 |
| 30 | 70 |
| 32 | 70 |
| 33 | 80 |
| 37 | 80 |
| 38 | 40 |

Chromatogram obtained by reverse phase HPLC is illustrated in FIG. 1. Each fraction was subjected to ESI-MS, and the target molecular ion peak was confirmed in the fraction 4 at $[M+H]^+$ m/z=867. The analytical result of the fraction 4 obtained by ESI-MS is illustrated in FIG. 2. Analytical conditions for ESI-MS are described below.
(Analytical Conditions for ESI-MS)
   Instrument for use: liquid chromatography time-of-flight mass spectrometer JMS-T100LC (manufactured by JEOL Ltd.)
   Solvent: solution A: ultra pure water/0.05% (v/v) TFA, solution B: $CH_3CN$/0.05% (v/v) TFA
   Flow rate: 0.2 ml/min
   Sample injection amount: about 5 µl
   Mixing ratio: solution B=20%
(8) The fraction 4 of reverse phase HPLC was concentrated and dried followed by freeze drying to obtain a cyclic peptide (cyclic Fmoc-CFWAH).

[Removal of N Terminal Protecting Group (Fmoc)]

The cyclic peptide that has been obtained by the above method was treated with piperidine for a short period of time to remove the N terminal protecting group (Fmoc).

(1) 0.1 mg of the cyclic Fmoc-CFWAH was dissolved in 20 μl DMF, and after being added with 20 μl of 20% (v/v) piperidine (manufactured by KOKUSAN CHEMICAL CO., LTD.)/DMF, it was allowed to stand for 3 minutes at room temperature.

(2) 360 μl of 15% (v/v) $CH_3CN$/1% (v/v) acetic acid (manufactured by Sigma Aldrich) was added thereto.

(3) The reaction solution was purified with Sep-pak (registered trademark) (C18) plus column (manufactured by Waters Corporation) to collect a fraction eluted with 60% (v/v) $CH_3CN$/ultra pure water.

(4) The sample was concentrated, dried, freeze-dried, and then dissolved in 1 ml of DMSO.

(5) The sample was purified by reverse phase HPLC. Conditions for reverse phase HPLC are as follows.

Instrument for use: LC-2000Plus series (manufactured by JASCO Corporation)

Column: Intertsil ODS-3 20×150 mm (manufactured by GL SCIENCES INC.)

Flow rate: 10 ml/min

Detection wavelength: 220 nm

TABLE 5

| Gradient condition | |
|---|---|
| Time (minutes) | $CH_3CN$ (%) |
| 0 | 20 |
| 40 | 60 |
| 42 | 60 |
| 43 | 80 |
| 45 | 80 |
| 46 | 20 |

Chromatogram obtained by reverse phase HPLC is illustrated in FIG. 3. Each fraction was subjected to ESI-MS, and the target molecular ion peak was confirmed in the fraction 32 at $[M+H]^+$ m/z=644. The analytical result of the fraction 32 obtained by ESI-MS is illustrated in FIG. 4. Analytical conditions for ESI-MS are as defined in the above.

(8) The fraction 32 of reverse phase HPLC was concentrated and dried followed by freeze drying to obtain a cyclic peptide having a thiolactone structure represented by Formula (1) (cyclic CFWAH).

Meanwhile, the peptide having 6 to 8 amino acid residues shown in Table 6 was also obtained as a cyclic peptide having thiolactone structure according to the same method as described above. In Table 6, cyclic Fmoc-CFWAH (peptide 5n) and peptide 6n correspond to the present invention.

Furthermore, when the deprotection time using piperidine in the step (1) is extended from 3 minutes to 15 minutes in the aforementioned synthetic method, a peptide having lactam structure represented by Formula (2) can be preferentially obtained.

[Inhibitory Activity of Cyclic CFWAH on Toxin Production by Clostridium welchii]

Clostridium welchii strain 13 (strain kept in Kanazawa University, Graduate School of Medical Sciences, Lecture of Microbial Infection Control) was cultured in 10 ml of TSF medium (trypton 40 g, soyton 4 g, fructose 5 g/L) for 6 hours at 37° C. After that, 500 μl of the culture was centrifuged (15,000 rpm×5 minutes) to collect the cells.

The cell pellet was re-suspended in 500 μl TSF medium. The cyclic peptide having 5 to 8 residues with thiolactone structure was dissolved in DMSO, and after being added to a medium to have final concentration of 10 μM for each, it was incubated for 2.5 hours at 37° C. Then, total RNA was prepared by hot phenol method. Specifically, by centrifuging 2 ml of Clostridium welchii culture at 15,000 rpm for 5 minutes, the supernatant was removed. The cells were suspended in 100 μl of the solution A which contains 20 mM sodium acetate, 1 mM EDTA, and 0.5% (w/v) SDS. Then, after blending with 100 μl of phenol saturated with citric acid (pH 4.3), it was shaken for 5 minutes in an incubator at 65° C. Subsequently, it was centrifuged for 5 minutes at 15,000 rpm to recover the aqueous layer and the RNA was precipitated by ethanol precipitation to prepare total RNA. The prepared total RNA was dissolved in 50 μl of water.

TABLE 6

| Name | Sequence | Number of residues | |
|---|---|---|---|
| Cyclic CFWAH (peptide 5n) | Cys-Phe-Trp-Ala-His | 5 | SEQ ID NO: 1 |
| Peptide 6n | Ala-Cys-Phe-Trp-Ala-His | 6 | SEQ ID NO: 5 |
| Peptide 7n | Ser-Ala-Cys-Phe-Trp-Ala-His | 7 | SEQ ID NO: 6 |
| Peptide 8n | Thr-Ser-Ala-Cys-Phe-Trp-Ala-His | 8 | SEQ ID NO: 7 |

(In all peptides above, thiolactone is formed between Cys residue and His residue)

By using theta-toxin (pfoA) gene probe, Northern blot analysis was performed. Specifically, the prepared total RNA (10 μg) was denatured with urea, separated by agarose electrophoresis, and transferred onto a nylon membrane. By using AlkPhos-Direct Labeling kit (GE Healthcare), the toxin gene DNA amplified by PCR (primers of SEQ ID NOS: 10 and 11 were used, template: genomic DNA of Clostridium welchii strain 13, polymerase: EX-Taq (manufactured by Takara Bio Inc.), PCR conditions: 98° C.×3 minutes, 98° C.×30 seconds→52° C.×30 seconds→68° C.×30 seconds, 30 cycles) was labeled. The gene on the nylon membrane was hybridized with the labeled DNA (probe) in Rapid-hyb buffer (GE Healthcare) for 2 hours at 55° C. The nylon membrane was washed with 2×SSPE buffer/0.1% (w/v) SDS and 0.7×SSC buffer/0.1% (w/v) SDS. CDPstar chemiluminescence method was employed for detection of signal.

Result of Northern blot analysis is illustrated in FIG. 5. In FIG. 5, lane 1 indicates the result from incubation in 10 ml of natural medium, lane 2 indicates the result from incubation in 500 μl of natural medium, lane 3 indicates the result from incubation with the addition of 10 μl of DMSO to the medium, and each of lane 4 to 7 indicates the result from incubation with the cyclic CFWAH (peptide 5n), peptide 6n, peptide 7n, or peptide 8n, that has been added to the medium to have final concentration of 10 μM. As illustrated in FIG. 5, the activity of inhibiting toxin expression was shown with the cyclic CFWAH (peptide 5n) or peptide 6n, and a particularly high activity was shown with the cyclic CFWAH (peptide 5n).

From the above, it was shown that the peptide represented by Formula (1) has an inhibitory activity on toxin production by a bacterium belonging to the genus *Clostridium*.

Example 2

According to the following method, the inhibitory activity of broth of *Clostridium butyricum* on toxin production by a bacterium belonging to the genus *Clostridium* was confirmed.

[Co-Culture Test]

*Clostridium welchii* strain 13, *Clostridium butyricum* miyairi 588 (*Clostridium butyricum* MIYAIRI 588, FERM BP-2789, obtained from MIYARISAN PHARMACEUTICAL CO., LTD.) or *Clostridium butyricum* ATCC19398 (purchased from ATCC) was cultured overnight at 37° C. in GAM medium (GAM bouillon (manufactured by Nissui Pharmaceutical Co., Ltd.), composition: in 59.0 g (corresponding to 1 L), peptone 10.0 g, soybean peptone 3.0 g, protease peptone 10.0 g, digested serum powder 13.5 g, yeast extract 5.0 g, meat extract 2.2 g, liver extract 1.2 g, glucose 3.0 g, potassium dihydrogen phosphate 2.5 g, sodium chloride 3.0 g, soluble starch 5.0 g, L-cysteine hydrochloride salt 0.3 g, and sodium thioglycolate 0.3 g, pH 7.1). Each 2 ml of the cultured broth was collected and centrifuged (15,000 rpm×5 minutes) to harvest cells. The cell pellet was washed twice with 2 ml of GAM medium and then suspended in 2 ml of GAM medium.

For co-culture, a culture plate with cups (THINCERTS, Greiner Bio-One, 657641) was used. The schematic diagram of the plates used for co-culture is illustrated in FIG. 6. The bottom surface of each well of the culture plate and the bottom surface of the cup inserted in each well are not in contact with each other. The bottom surface of the cup is composed of a membrane with pore size of 0.4 µm so that the upper layer (within cup) and the lower layer (region below the bottom surface of the cup) in the well were partitioned by a membrane with pore size of 0.4 µm.

To the lower layer in culture well, 4.5 ml of GAM medium and 500 µl of the suspension of *Clostridium butyricum* prepared above (*Clostridium butyricum* miyairi 588 or *Clostridium butyricum* ATCC19398) were added. As a control, 500 µl of GAM medium was added into the lower layer of other well, instead of the above suspension of *Clostridium butyricum*. To an upper layer in the well, 4.5 ml of GAM medium was added followed by anaerobic culture at 37° C. Among the materials produced by *Clostridium butyricum*, materials that can pass through the membrane diffused into the GAM medium in the upper layer during the anaerobic culture.

After culturing for 5 or 7 hours, 500 µl of *Clostridium welchii* that has been prepared above was added onto the upper layer, and then again subjected to anaerobic culture (co-culture) at 37° C. 2 hours and 3 hours after start of the co-culture, total RNA was prepared from *Clostridium welchii* on the cup by using a hot phenol method.

[Microarray Analysis]

Microarray analysis was performed according to the method by Ohtani et al. (Ohtani, K. et al., Anaerobe (2010), 16: 258-264). Specifically, the total RNA prepared from control *Clostridium welchii* and the total RNA prepared from *Clostridium welchii* that has been co-cultured with *Clostridium butyricum* were labeled with Cy5 and Cy3, respectively. The fluorescent pigment Cy3 and Cy5 were purchased from GE Healthcare. For the labeling reaction, SuperScript Indirect cDNA labeling kit (manufactured by Invitrogen) was used.

The labeled RNA was hybridized to the *Clostridium welchii* custom DNA microarray (provided by Professor Satoru Kuhara at Faculty of Agriculture, Kyushu University). As for the microarray, an array with accession number GPL9765 of GEO database (http://www.ncbi.nlm.nih.gov/geo/) was used. Fluorescence intensities of the DNA spots for each gene on microarray were measured by a scanner for microarray (manufactured by FUJIFILM Corporation), and the expression ratio of each gene (co-culture/control) was calculated. For data analysis, R and limma (Linear Model for Microarray Data) software was used, and when p value is less than 0.05, it was considered that there is a significant change in gene expression.

Part of the result of the microarray experiment when *Clostridium welchii* was added onto the upper layer after culturing for 5 hours is shown in Table 7. In Table 7, the underlined number indicates that the gene expression is significantly inhibited when co-cultured with *Clostridium butyricum*. It is demonstrated that the material diffused from a broth of *Clostridium butyricum* acted on *Clostridium welchii* so that expression of those genes were inhibited.

TABLE 7

| CPE# | Gene name | *Clostridium butyricum* ATCC | | *Clostridium butyricum* miyairi 588 | |
|---|---|---|---|---|---|
| | | Co-culture for 2 hours | Co-culture for 3 hours | Co-culture for 2 hours | Co-culture for 3 hours |
| CPE0036 | plc | 0.58 | 0.77 | <u>0.31</u> | <u>0.37</u> |
| CPE0173 | colA | 0.79 | 1.13 | <u>0.32</u> | <u>0.42</u> |
| CPE0319 | fucA | 0.54 | <u>0.16</u> | <u>0.30</u> | <u>0.15</u> |
| CPE0320 | CPE0320 | 0.52 | <u>0.20</u> | <u>0.35</u> | <u>0.15</u> |
| CPE0321 | CPE0321 | 0.56 | <u>0.14</u> | <u>0.41</u> | <u>0.19</u> |
| CPE0325 | CPE0325 | 0.53 | <u>0.17</u> | <u>0.29</u> | <u>0.16</u> |
| CPE0326 | lacA | 0.63 | <u>0.24</u> | <u>0.43</u> | <u>0.19</u> |
| CPE0327 | lacB | 0.54 | <u>0.16</u> | <u>0.48</u> | <u>0.17</u> |
| CPE0374 | aga | 0.80 | <u>0.21</u> | <u>0.39</u> | <u>0.11</u> |
| CPE0390 | dchS | 0.58 | 1.47 | <u>0.49</u> | <u>0.43</u> |
| CPE0423 | pcrA | 0.60 | 0.66 | <u>0.41</u> | <u>0.35</u> |
| CPE0904 | eutT | 0.61 | <u>0.39</u> | <u>0.44</u> | <u>0.28</u> |
| CPE0906 | CPE0906 | 0.56 | <u>0.40</u> | <u>0.46</u> | <u>0.25</u> |
| CPE1142 | CPE1142 | 0.55 | <u>0.23</u> | <u>0.42</u> | <u>0.39</u> |

The underlined numbers indicate inhibited gene expression.

In the group of genes with inhibited expression, genes encoding toxin such as alpha-toxin (plc) or kappa-toxin (colA) were included.

[Northern Blot Analysis]

Inhibition of gene expression determined by above microarray was validated by Northern blot analysis.

Meanwhile, the Northern blot analysis was performed by the aforementioned method. As a gene probe, the followings were used: alpha-toxin prepared by the aforementioned PCR method (plc, primers of SEQ ID NOS: 12 and 13 are used), theta-toxin (pfoA, primers of SEQ ID NOS: 10 and 11 are used), kappa-toxin (colA, primers of SEQ ID NOS: 14 and 15 are used), toxin regulating RNA (VR-RNA, VR in FIG. 7, primers of SEQ ID NOS: 16 and 17 are used), and a gene regulated by VirR/VirS system (CPE0845, 0845 in FIG. 7, primers of SEQ ID NOS: 18 and 19 are used).

Result of the Northern blot analysis is illustrated in FIG. 7. In FIG. 7, "GAM" lane indicates the result of a case where GAM medium is added to the lower layer, "st13" indicates the result of a case where *Clostridium welchii* is cultured alone, "Miya" indicates the result of a case where it is co-cultured with *Clostridium butyricum* miyairi 588, and "ATCC" lane indicates the result of a case where it is co-cultured with *Clostridium butyricum* ATCC19398. Furthermore, "A5" and "B5" indicate the result when *Clostridium welchii* was added onto the upper layer after culturing for 5 hours. Furthermore, "A7" and "B7" indicate the result when *Clostridium welchii* was added onto the upper layer after culturing for 7 hours.

As illustrated in FIG. 7, it was confirmed that expressions of all genes were markedly reduced by the co-culture with *Clostridium butyricum*.

From the above, it was confirmed that the component secreted from *Clostridium butyricum* into the medium inhibits toxin production by a bacterium belonging to the genus *Clostridium*. As such, it was shown that the broth of *Clostridium butyricum* has an inhibitory activity on toxin production by a bacterium belonging to the genus *Clostridium*. Furthermore, from FIG. 7, it was found that the inhibitory activity on toxin production by a bacterium belonging to the genus *Clostridium* is particularly excellent in *Clostridium butyricum* miyairi 588.

[Inhibited Toxin Gene Expression by *Clostridium butyricum* agrD Gene]

The *Clostridium butyricum* agrD gene was expressed in *Clostridium welchii*, and the effect on toxin gene expression in *Clostridium welchii* was determined.

The DNA fragment of agrD region in *Clostridium butyricum* was prepared by PCR. As a polymerase, KOD (manufactured by TOYOBO CO., LTD.) was used, and it was amplified at following conditions; 95° C.×3 minutes, 98° C.×10 seconds→52° C.×30 seconds→68° C.×2 minutes, 30 cycles. Meanwhile, as a template, genomic DNA extracted from *Clostridium butyricum* miyairi 588 was used. DNA preparation was carried out by a standard method. The followings were used as a primer.

```
Chem. 9
agrdbu primer 1
                                    (SEQ ID NO: 8)
TTGGATCCTCATTGGTACACAGAAAAAC agrdbu primer 2
                                    (SEQ ID NO: 9)
AAAAGCTTATGGGATGCTGGTATCTGAG
```

The PCR-amplified product was treated with the restriction enzyme SmaI and cloned into a shuttle vector pJIR 418 for *Clostridium welchii* and *E. coli*.

A plasmid ("agrbu" in FIG. 8) having agrD gene of *Clostridium butyricum* or the shuttle vector before recombination ("418" in FIG. 8) was introduced by electroporation into *Clostridium welchii* strain 13 (wild type strain, "13/" in FIG. 8) or agrD variant strain (derived from *Clostridium welchii* strain 13, "TS230/" in FIG. 8). Because a chloramphenicol-resistance gene is encoded in the vector, after electroporation, colonies of *Clostridium welchii* having plasmid were screened with chloramphenicol.

After the electroporation, *Clostridium welchii* was cultured in GAM medium at 37° C. 3 hours after start of the culture, total RNA was prepared by the method described above. According to the above method, Northern blot analysis was performed to confirm the gene expression. The results are illustrated in FIG. 8.

From FIG. 8, it was confirmed that by expressing *Clostridium butyricum* agrD gene in *Clostridium welchii*, expression of pfoA, colA, and plc in *Clostridium welchii* is inhibited.

From the above, it was found that AgrD of *Clostridium butyricum* can inhibit the toxin production in a bacterium belonging to the genus *Clostridium*.

Example 3

According to the following method, peptide represented by Formula (1) (AgrD$_{cb}$-thiolactone) and peptide represented by Formula (2) (AgrD$_{cb}$-lactam) were synthesized, and their inhibitory activities of toxin production against *Clostridium welchii* were determined.

[Synthesis of AgrD$_{cb}$-Thiolactone]

(1) A chemically synthesized peptide bound to TrtResin (Trt (2-Cl)-resin)/Z group (benzyloxycarbonyl group) (Z group-CFWAH-TrtResin) was purchased from Scrum Inc. 290 mg of dry peptide bound to resin was added to 10 ml of the cleavage cocktail with above composition, and stirred for 5 hours at room temperature. Then, the resin was removed in the same manner as Example 1 to give a linear peptide having Z group from which the resin has been removed.

(2) By using the linear peptide having Z group, a dehydrating cyclization reaction using PyBOP was performed in the same manner as Example 1. Accordingly, cyclic Z group-CFWAH was obtained.

(3) Next, by using TFA/thioanisole, the Z group as an N terminal protecting group was removed. Specifically, 11 mg of the above cyclic Z group-CFWAH was added to the following cleavage cocktail (2), and stirred for 12.5 hours at room temperature.

TABLE 8

| Composition of cleavage cocktail (2) | |
|---|---|
| TFA (manufactured by Kanto Chemical Co., Inc.) | 7560 µl |
| Thioanisole (manufactured by Merck KGaA) | 760 µl |
| 1,2-Ethane dithiol (manufactured by Tokyo Chemical Industry Co., Ltd.) | 760 µl |
| Anhydrous TFA (manufactured by Merck KGaA) | 160 µl |
| m-Cresol (manufactured by NACALAI TESQUE, INC.) | 760 µl |

(4) The reaction solution was added dropwise to 200 ml of ice cold 5% (v/v) CH$_3$CN/ultra pure water/0.1% (v/v) TFA, and the reaction was terminated.

(5) The reaction solution was purified with Sep-pak (registered trademark) (C18) plus column (manufactured by Waters Corporation) to collect a fraction eluted with 30% (v/v) CH$_3$CN/ultra pure water/0.1% (v/v) TFA.

(6) The sample was concentrated, dried, and freeze-dried and dissolved in DMSO.

(7) After purified by reverse phase HPLC at above conditions, and the sample was dried to solid to give AgrD$_{cb}$-thiolactone (CFWAH).

[Synthesis of AgrD$_{cb}$-Lactam]

Next, the peptide (AgrD$_{cb}$-lactam) represented by Formula (2) was synthesized by an alkali conversion reaction.

(1) AgrD$_{cb}$-thiolactone that has been synthesized by the above method was dissolved in DMSO to prepare 10 µg/µl solution, and diluted to 3 µg/µl solution by adding ultra pure water.

(2) 10 µl of 28% (w/w) aqueous ammonia solution was added to 10 µl of the above solution, and the reaction was allowed to occur for 30 minutes at 37° C.

(3) The reaction was terminated by adding 120 µl of 0.05% (v/v) TFA aqueous solution, and pH was adjusted to about 7 with 5% acetic acid.

(4) Purification was performed by reverse phase HPLC at above conditions, and each obtained fraction was analyzed by ESI-MS to collect a fraction containing the target m/z=645.

(5) The obtained peptide fraction was dried to solid to give AgrD$_{cb}$-lactam (CFWAH).

[Inhibiting Activity of Cyclic CFWAH on Toxin Production by *Clostridium welchii*]

The inhibitory activities on toxin production by *Clostridium welchii* were evaluated for $AgrD_{cb}$-thiolactone and $AgrD_{cb}$-lactam.

*Clostridium welchii* strain 13 was cultured for 5 hours at 37° C. in 2 ml of GAM medium. The culture of *Clostridium welchii* was added to TSF medium containing $AgrD_{cb}$-thiolactone or $AgrD_{cb}$-lactam at final concentration of 10 µM, and cultured for 2.5 hours at 37° C. Then, the brothes were centrifuged to collect the cells, and total RNA were prepared in the same manner as Example 1. As a control, total RNA prepared from *Clostridium welchii*, which has been cultured in a medium without any peptide according to the present invention, was used.

By performing quantitative PCR, expression of the gene encoding theta-toxin (pfoA) in *Clostridium welchii* was evaluated. Meanwhile, for the quantitative PCR, primers of SEQ ID NO: 27 (TGAAGCACCTCCACTTATGG) and SEQ ID NO: 28 (GCATCTCCTCCTAAAACTACTG), and One Step SYBR (registered trademark) PrimeScript RT-PCR Kit II (Perfect Real Time) (manufactured by Takara Bio Inc.) were used. As a housekeeping gene, 16S rRNA was used (SEQ ID NO: 29: AGTTACAGTCCAGAGAGTCG, SEQ ID NO: 30: TATCTAGAGTGCAGGAGAGG). The measurement was carried out by real time PCR system Mx3000P QPCR System (manufactured by Agilent Technologies, Inc.) at conditions as follows: 42° C.×5 minutes→95° C.×10 seconds→(95° C.×5 seconds→60° C.×20 seconds→72° C.×32 seconds)×40 cycles. The results are illustrated in FIG. 9.

As illustrated in FIG. 9, it was found that the expression of the gene encoding theta-toxin (pfoA) in *Clostridium welchii* was inhibited by $AgrD_{cb}$-thiolactone and AgrDcb-lactam. By having the expression amount of the gene which encodes *Clostridium welchii* theta-toxin (pfoA) as an indicator, $IC_{50}$ of the inhibitory activity on the toxin production was determined for $AgrD_{cb}$-thiolactone and AgrDcb-lactam. As a result, it was found to be 10 µM for both.

$AgrD_{cb}$-thiolactone is advantageous in that it can be obtained with only a few numbers of steps. On the other hand, $AgrD_{cb}$-lactam is advantageous in that it is structurally more stable than $AgrD_{cb}$-thiolactone Example 4

Based on the method of Example (3), a cyclic peptide having thiolactone structure in which each of $R^1$ and $X^1$ to $X^4$ in Formula (1) is an amino acid shown in Table 9 was synthesized, and the expression of the gene which encodes *Clostridium welchii* theta-toxin (pfoA) was measured by quantitative PCR. Meanwhile, the peptide linked with Z group (benzyloxycarbonyl group) of Table 9 was obtained by performing the above-described dehydrating cyclization reaction using PyBOP, without treating with TFA/thioanisole, and performing purification with Sep-pak (registered trademark) (C18) plus column (manufactured by Waters Corporation) and reverse phase HPLC.

By having the expression amount of the gene which encodes *Clostridium welchii* theta-toxin (pfoA) as an indicator, $IC_{50}$ of the inhibitory activity on the toxin production was measured for each cyclic peptide. Meanwhile, in Table 9, "agonist" means increased expression of pfoA gene (it has an agonistic activity), and "No activity" means that neither the inhibitory activity on the toxin production (antagonist activity) nor agonist activity was found.

TABLE 9

| $R^1$ | SEQ ID NO. | $X^1$ | $X^2$ | $X^3$ | $X^4$ | Protecting group for carboxyl group of $X^4$ | IC50 (µM) | |
|---|---|---|---|---|---|---|---|---|
| Benzyloxycarbonyl group | 33 | Ala | Trp | Ala | Ala | — | 5 | Present invention |
| Benzyloxycarbonyl group | 20 | Ala | Trp | Phe | Ala | — | 0.3 | Present invention |
| Benzyloxycarbonyl group | 37 | Ala | Trp | Phe | Thr | — | (No activity) | Comparative Example |
| Benzyloxycarbonyl group | 38 | Leu | Trp | Phe | Ala | — | (Agonist) | Comparative Example |
| Benzyloxycarbonyl group | 31 | Leu | Trp | Ala | Thr | — | 5 | Present invention |
| Benzyloxycarbonyl group | 39 | Leu | Ala | Phe | Thr | — | (No activity) | Comparative Example |
| Benzyloxycarbonyl group | 22 | Leu | Phe | Trp | Thr | — | 5 | Present invention |
| Benzyloxycarbonyl group | 21 | Leu | Trp | Phe | Ser | — | 5 | Present invention |
| Benzyloxycarbonyl group | 40 | Leu | Trp | Phe | Thr | Benzyl group | (Agonist) | Comparative Example (amino acid sequence of *Clostridium welchii*) |
| Benzyloxycarbonyl group | 41 | Leu | Trp | Tyr | Thr | — | (Agonist) | Comparative Example |
| Benzyloxycarbonyl group | 42 | Leu | Phe | Trp | Ser | — | (No activity) | Comparative Example |
| Hydrogen atom | 21 | Leu | Trp | Phe | Ser | — | 5 | Present invention |
| Hydrogen atom | 22 | Leu | Phe | Trp | Thr | — | 0.5 | Present invention |
| Hydrogen atom | 41 | Leu | Trp | Tyr | Thr | — | (Agonist) | Comparative Example |
| Hydrogen atom | 20 | Ala | Trp | Phe | Ala | — | 0.3 | Present invention |
| Hydrogen atom | 40 | Leu | Trp | Phe | Thr | Benzyl group | (Agonist) | Comparative Example (amino acid sequence of *Clostridium welchii*) |
| Benzyloxycarbonyl group | 35 | Leu | Trp | Ala | Ser | — | 1 | Present invention |

It is considered to be necessary for exhibition of an agonist activity or an antagonist activity that the peptide can bind to VirS (peptide having a binding activity). In Table 9, the agonist activity was observed from Z group-CLWFT-Bzl group (amino acid sequence of *Clostridium welchii*) and Z group-CLWFA, and the antagonist activity was observed from Z group-CAWAA, Z group-CLWAT, and Z group-CLFWT, while neither the agonist activity nor antagonist activity was observed for Z group-CLAFT. From these results, it is believed that, when $X^2$ is an aromatic amino acid, the binding activity for VirS is improved.

Z group-CLWFT-Bzl group (amino acid sequence of *Clostridium welchii*) was an agonist while Z group-CLWFS was an antagonist. From these results, it is believed that $X^4$ needs to be Thr to have an agonist activity.

Example 5

It was confirmed that *Clostridium butyricum* secretes AgrD extracellularly.

First, culture was performed at following conditions, and a sample for analysis was collected. Specifically, a single colony of *Clostridium butyricum* MIYAIRI 588 was inoculated to 10 mL of brain heart infusion medium (BHI medium) (manufactured by BD), and cultured overnight at 37° C. in an anaerobic chamber (nitrogen 80%/hydrogen 10%/carbon dioxide 10%). The broth was inoculated (1%) to 600 mL of BHI medium (1 L conical flask was used), and cultured (37° C.) in an anaerobic chamber. During the culture, OD660 nm was measured over time, and the broth was collected at following timings: when OD660 nm is 0.209 (culture for 3.75 hours, initial phase of exponential growth, a in FIG. 10), when OD660 nm is 0.660 (culture for 4.5 hours, middle phase of exponential growth, b in FIG. 10), when OD660 nm is 1.648 (culture for 5.1 hours, later phase of exponential growth, c in FIG. 10), and when OD660 nm is 1.130 (culture for 24 hours, stationary phase of exponential growth, d in FIG. 10). For collection, 120 mL of the broth was sampled, centrifuged for 10 minutes at 5000×g, and the supernatant was collected and used as a sample for analysis. A change in OD value during the culture was illustrated in FIG. 10.

Next, 10 μl of aqueous ammonia solution (28% (w/w)) and 1.5 μl of 2-mercaptoethanol were added to 0.4 ml of the culture supernatant collected in the above, and incubated for 3 hours at 37° C. (ammonia treatment). After adding 120 μl of 0.05% (v/v) TFA to the reaction solution for neutralization, 60 μl of ethyl acetate was added, mixed under stirring, and centrifuged at 8000 rpm×5 minutes (4° C.). The ethyl acetate layer was collected, ethyl acetate was removed by distillation, and the collected solid was dissolved in 50 μl of DMSO and used for ESI-MS analysis.

(Analytical Conditions for ESI-MS)

Instrument for use: liquid chromatography time-of-flight mass spectrometer JMS-T100LC (manufactured by JEOL Ltd.)

Column: ZORBAX Eclipse XDB-C18, 5 μm, 2.1×50 mm (manufactured by Agilent Technologies, Inc.)

Solvent: solution A: ultra pure water/0.05% (v/v) TFA, solution B: $CH_3CN$/0.05% (v/v) TFA Detection mass number: m/z=645

Flow rate: 0.2 ml/min

Conditions for HPLC elution

TABLE 10

| Gradient condition | |
|---|---|
| Time (minutes) | $CH_3CN$ (%) |
| 0 | 10 |
| 5 | 10 |
| 55 | 35 |
| 60 | 90 |
| 65 | 90 |
| 67 | 10 |

Results of the ESI-MS analysis are illustrated in FIG. 11, and each of a to d in FIG. 11 indicates a sample that has been collected at time points of a to d in FIG. 10.

As illustrated in FIG. 11, the desired peak was detected at m/z=645 after the middle phase of exponential growth. The peak intensity continued to increase during the later phase of exponential growth, and the peak with the same intensity was also detected in the stationary phase. Meanwhile, when the analysis was performed in the same manner as above without treating the broth with ammonia, the desired peak was not detected at m/z=645. Thus, it is believed that the peak at m/z=645 corresponds to the lactam that was converted by the aforementioned ammonia treatment from the cyclic CFWAH (thiolactone) that has been secreted into the broth.

Therefore, it is believed that the cyclic CFWAH (thiolactone) is secreted to the broth by *Clostridium butyricum* MIYAIRI 588.

In this regard, it is believed that, as the broth of *Clostridium butyricum* containing the secreted cyclic CFWAH (thiolactone) functions probably as an antagonist for VirS, it can inhibit the toxin production by *Clostridium welchii*.

The examples and descriptions of preferred embodiments do not limit the present invention that is defined by the claims, and they need to be understood as an exemplification of the invention. All publications cited in the present specification are incorporated herein by reference in their entirety. As easily understandable, various modifications and combinations of the aforementioned features may be employed without deviating from the scope of the present invention claimed in the claims. Such modifications shold not be considered to be outside of the present invention, and all of such modifications are intended to be included in the claims.

The present application is based on Japanese Patent Application No. 2014-022811 filed on Feb. 7, 2014 and Japanese Patent Application No. 2014-211962 filed on Oct. 16, 2014, and the disclosures of which are entirely incorporated herein by reference.

Sequence Listing Free Text

[SEQ ID NO: 5]

Cyclic peptide consisting of 6 amino acid residues.

[SEQ ID NO: 6]

Cyclic peptide consisting of 7 amino acid residues.

[SEQ ID NO: 7]

Cyclic peptide consisting of 8 amino acid residues.

[SEQ ID NO: 8]

PCR primer sequence for amplification of DNA fragment including *Clostridium butylicum* agrD.

[SEQ ID NO: 9]

PCR primer sequence for amplification of DNA fragment including *Clostridium butylicum* agrD.

[SEQ ID NO: 10]

PCR primer sequence for amplification of DNA fragment including *Clostridium perfringens* pfoA.

[SEQ ID NO: 11]
PCR primer sequence for amplification of DNA fragment including *Clostridium perfringens* pfoA.
[SEQ ID NO: 12]
PCR primer sequence for amplification of DNA fragment including *Clostridium perfringens* plc.
[SEQ ID NO: 13]
PCR primer sequence for amplification of DNA fragment including *Clostridium perfringens* plc.
[SEQ ID NO: 14]
PCR primer sequence for amplification of DNA fragment including *Clostridium perfringens* colA.
[SEQ ID NO: 15]
PCR primer sequence for amplification of DNA fragment including *Clostridium perfringens* colA.
[SEQ ID NO: 16]
PCR primer sequence for amplification of DNA fragment including *Clostridium perfringens* VR-RNA.
[SEQ ID NO: 17]
PCR primer sequence for amplification of DNA fragment including *Clostridium perfringens* VR-RNA.
[SEQ ID NO: 18]
PCR primer sequence for amplification of DNA fragment including *Clostridium perfringens* CPE0845.
[SEQ ID NO: 19]
PCR primer sequence for amplification of DNA fragment including *Clostridium perfringens* CPE0845.
[SEQ ID NO: 27]
Primer sequence for quantitative PCR of *Clostridium perfringens* pfoA.
[SEQ ID NO: 28]
Primer sequence for quantitative PCR of *Clostridium perfringens* pfoA.
[SEQ ID NO: 29]
Primer sequence for quantitative PCR of *Clostridium perfringens* 16S rRNA.
[SEQ ID NO: 30]
Primer sequence for quantitative PCR of *Clostridium perfringens* 16S rRNA.

The invention claimed is:

1. A peptide represented by the following Formula (1):

[Chem. 1]

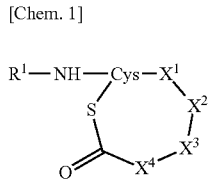

(1)

in Formula (1), $R^1$ is selected from the group consisting of an amino acid, ornithine, sarcosine, desmosine, isodesmosine, hydroxylysine, 3-hydroxyproline, 4-hydroxyproline, 2-aminoadipic acid, 3-aminoadipic acid, β-alanine, β-aminopropionic acid, 2-aminobutyric acid, 4-aminobutyric acid, 6-aminocaproic acid, 2-aminoheptanoic acid, 2-aminoisobutyric acid, and 3-aminoisobutyric acid, substituted or unsubstituted acyl group having 1 to 10 carbon atoms, substituted or unsubstituted benzyloxycarbonyl group, substituted or unsubstituted 9-fluorenylmethyloxycarbonyl group or substituted or unsubstituted phenylisothiocyanate group, and $X^1$, $X^2$, $X^3$ and $X^4$ are represented by any one of (1-1) to (1-4):

(1-1) $X^1$ is Ala, Gly, Trp, Phe, Val, Leu, Ile, or Tyr; $X^2$ is Phe, Trp or Tyr; $X^3$ is Ala; and $X^4$ is His, Ala, Thr or Ser, with the proviso that, when $X^2$ is Phe, $X^4$ is Thr, and when $X^4$ is Ala, $X^1$ is Ala;

(1-2) $X^1$ is Ala, $X^2$ is Trp, $X^3$ is Phe, and $X^4$ is Ala;

(1-3) $X^1$ is Leu, $X^2$ is Trp, $X^3$ is Phe, and $X^4$ is Ser; and (1-4) $X^1$ is Leu, $X^2$ is Phe, $X^3$ is Trp, and $X^4$ is Thr.

2. The peptide according to claim 1, wherein $R^1$ in Formula (1) is a benzyloxycarbonyl group.

3. A peptide represented by the following Formula (2):

[Chem. 2]

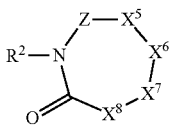

(2)

in Formula (2), $R^2$ is selected from the group consisting of an amino acid, ornithine, sarcosine, desmosine, isodesmosine, hydroxylysine, 3-hydroxyproline, 4-hydroxyproline, 2-aminoadipic acid, 3-aminoadipic acid, β-alanine, β-aminopropionic acid, 2-aminobutyric acid, 4-aminobutyric acid, 6-aminocaproic acid, 2-aminoheptanoic acid, 2-aminoisobutyric acid, and 3-aminoisobutyric acid, substituted or unsubstituted acyl group having 1 to 10 carbon atoms, substituted or unsubstituted benzyloxycarbonyl group, substituted or unsubstituted 9-fluorenylmethyloxycarbonyl group or substituted or unsubstituted phenylisothiocyanate group, Z is Cys, and $X^5$, $X^6$, $X^7$ and $X^8$ are represented by any one of (2-1) to (2-4):

(2-1) $X^5$ is Ala, Gly, Trp, Phe, Val, Leu, Ile, or Tyr; $X^6$ is Phe, Trp or Tyr; $X^7$ is Ala; and $X^8$ is His, Ala, Thr or Ser, with the proviso that, when $X^6$ is Phe, $X^8$ is Thr, and when $X^8$ is Ala, $X^5$ is Ala;

(2-2) $X^5$ is Ala, $X^6$ is Trp, $X^7$ is Phe, and $X^8$ is Ala;

(2-3) $X^5$ is Leu, $X^6$ is Trp, $X^7$ is Phe, and $X^8$ is Ser; and (2-4) $X^5$ is Leu, $X^6$ is Phe, $X^7$ is Trp, and $X^8$ is Thr.

4. The peptide according to claim 3, wherein $R^2$ in Formula (2) is a benzyloxycarbonyl group.

5. A method for inhibiting a toxin production by a bacterium belonging to a genus *Clostridium* using a peptide represented by the following Formula (1) or Formula (2):

[Chem. 1]

$$R^1-NH-Cys-X^1 \atop \underset{O}{\overset{S}{\diagdown}}\!\!\!\!\!\diagup\!\!\!\!\!\underset{X^4}{\diagdown}\!\!\!\underset{X^3}{\overset{X^2}{\diagup}} \tag{1}$$

in Formula (1), $R^1$ is selected from the group consisting of an amino acid, ornithine, sarcosine, desmosine, isodesmosine, hydroxylysine, 3-hydroxyproline, 4-hydroxyproline, 2-aminoadipic acid, 3-aminoadipic acid, β-alanine, β-aminopropionic acid, 2-aminobutyric acid, 4-aminobutyric acid, 6-aminocapronic acid, 2-aminoheptanoic acid, 2-aminoisobutyric acid, and 3-aminoisobutyric acid, substituted or unsubstituted acyl group having 1 to 10 carbon atoms, substituted or unsubstituted benzyloxycarbonyl group, substituted or unsubstituted 9-fluorenylmethyloxycarbonyl group or substituted or unsubstituted phenylisothiocyanate group, and $X^1$, $X^2$, $X^3$ and $X^4$ are represented by any one of (1-1) to (1-4):
(1-1) $X^1$ is Ala, Gly, Trp, Phe, Val, Leu, Ile, or Tyr; $X^2$ is Phe, Trp or Tyr; $X^3$ is Ala;
and $X^4$ is His, Ala, Thr or Ser, with the proviso that, when $X^2$ is Phe, $X^4$ is Thr, and when $X^4$ is Ala, $X^1$ is Ala;
(1-2) $X^1$ is Ala, $X^2$ is Trp, $X^3$ is Phe, and $X^4$ is Ala;
(1-3) $X^1$ is Leu, $X^2$ is Trp, $X^3$ is Phe, and $X^4$ is Ser; and
(1-4) $X^1$ is Leu, $X^2$ is Phe, $X^3$ is Trp, and $X^4$ is Thr;

[Chem. 2]

$$R^2-N \atop \underset{O}{\overset{Z}{\diagdown}}\!\!\!\!\!\diagup\!\!\!\!\!\underset{X^8}{\diagdown}\!\!\!\underset{X^7}{\overset{X^6}{\diagup}}\!\!\underset{X^5}{} \tag{2}$$

in Formula (2), $R^2$ is selected from the group consisting of an amino acid, ornithine, sarcosine, desmosine, isodesmosine, hydroxylysine, 3-hydroxyproline, 4-hydroxyproline, 2-aminoadipic acid, 3-aminoadipic acid, β-alanine, β-aminopropionic acid, 2-aminobutyric acid, 4-aminobutyric acid, 6-aminocapronic acid, 2-aminoheptanoic acid, 2-aminoisobutyric acid, and 3-aminoisobutyric acid, substituted or unsubstituted acyl group having 1 to 10 carbon atoms, substituted or unsubstituted benzyloxycarbonyl group, substituted or unsubstituted 9-fluorenylmethyloxycarbonyl group or substituted or unsubstituted phenylisothiocyanate group, Z is Cys, wherein X and $X^5$, $X^6$, $X^7$ and $X^8$ are represented by any one of (2-1) to (2-4):
(2-1) $X^5$ is Ala, Gly, Trp, Phe, Val, Leu, Ile, or Tyr; $X^6$ is Phe, Trp or Tyr; $X^7$ is Ala;
and $X^8$ is His, Ala, Thr or Ser, with the proviso that, when $X^6$ is Phe, $X^8$ is Thr, and when $X^8$ is Ala, $X^5$ is Ala;
(2-2) $X^5$ is Ala, $X^6$ is Trp, $X^7$ is Phe, and $X^8$ is Ala;
(2-3) $X^5$ is Leu, $X^6$ is Trp, $X^7$ is Phe, and $X^8$ is Ser; and
(2-4) $X^5$ is Leu, $X^6$ is Phe, $X^7$ is Trp, and $X^8$ is Thr.

6. A method for inhibiting a toxin production by a bacterium belonging to a genus *Clostridium* using a cultured broth of *Clostridium butyricum* or a dried product of the broth,
wherein the bacterium belonging to the genus *Clostridium* is *Clostridium* welchii (*Clostridium perfringens*).

7. The method according to claim 6, wherein *Clostridium butyricum* is *Clostridium butyricum* miyairi 588 (*Clostridium butyricum* MIYAIRI 588, FERM BP-2789).

8. The method according to claim 5, wherein the bacterium belonging to the genus *Clostridium* is *Clostridium* welchii (*Clostridium perfringens*).

9. A pharmaceutical composition, or a food product, or an animal feed comprising a toxin production inhibitor comprising, as an effective ingredient, a peptide represented by the following Formula (1) or Formula (2):

$$R^1-NH-Cys-X^1 \atop \underset{O}{\overset{S}{\diagdown}}\!\!\!\!\!\diagup\!\!\!\!\!\underset{X^4}{\diagdown}\!\!\!\underset{X^3}{\overset{X^2}{\diagup}} \tag{1}$$

in Formula (1), $R^1$ is selected from the group consisting of an amino acid, ornithine, sarcosine, desmosine, isodesmosine, hydroxylysine, 3-hydroxyproline, 4-hydroxyproline, 2-aminoadipic acid, 3-aminoadipic acid, β-alanine, β-aminopropionic acid, 2-aminobutyric acid, 4-aminobutyric acid, 6-aminocapronic acid, 2-aminoheptanoic acid, 2-aminoisobutyric acid, and 3-aminoisobutyric acid, substituted or unsubstituted acyl group having 1 to 10 carbon atoms, substituted or unsubstituted benzyloxycarbonyl group, substituted or unsubstituted 9-fluorenylmethyloxycarbonyl group or substituted or unsubstituted phenylisothiocyanate group, and $X^1$, $X^2$, $X^3$ and $X^4$ are represented by any one of (1-1) to (1-4):
(1-1) $X^1$ is Ala, Gly, Trp, Phe, Val, Leu, Ile, or Tyr; $X^2$ is Phe, Trp or Tyr; $X^3$ is Ala;
and $X^4$ is His, Ala, Thr or Ser, with the proviso that, when $X^2$ is Phe, $X^4$ is Thr, and when $X^4$ is Ala, $X^1$ is Ala;
(1-2) $X^1$ is Ala, $X^2$ is Trp, $X^3$ is Phe, and $X^4$ is Ala;
(1-3) $X^1$ is Leu, $X^2$ is Trp, $X^3$ is Phe, and $X^4$ is Ser; or
(1-4) $X^1$ is Leu, $X^2$ is Phe, $X^3$ is Trp, and $X^4$ is Thr;

$$R^2-N \atop \underset{O}{\overset{Z}{\diagdown}}\!\!\!\!\!\diagup\!\!\!\!\!\underset{X^8}{\diagdown}\!\!\!\underset{X^7}{\overset{X^6}{\diagup}}\!\!\underset{X^5}{} \tag{2}$$

in Formula (2), $R^2$ is an amino acid, substituted or unsubstituted acyl group having 1 to 10 carbon atoms, substituted or unsubstituted benzyloxycarbonyl group, substituted or unsubstituted 9-fluorenylmethyloxycarbonyl group or substituted or unsubstituted phenylisothiocyanate group, Z is Cys, and $X^5$, $X^6$, $X^7$ and $X^8$ are represented by any one of (2-1) to (2-4):
(2-1) $X^5$ is Ala, Gly, Trp, Phe, Val, Leu, Ile, or Tyr; $X^6$ is Phe, Trp or Tyr; $X^7$ is Ala;
and $X^8$ is His, Ala, Thr or Ser, with the proviso that, when $X^6$ is Phe, $X^8$ is Thr, and when $X^8$ is Ala, $X^5$ is Ala;
(2-2) $X^5$ is Ala, $X^6$ is Trp, $X^7$ is Phe, and $X^8$ is Ala;

(2-3) $X^5$ is Leu, $X^6$ is Trp, $X^7$ is Phe, and $X^8$ is Ser; and
(2-4) $X^5$ is Leu, $X^6$ is Phe, $X^7$ is Trp, and $X^8$ is Thr.

10. A method for treating infections caused by a bacterium belonging to genus *Clostridium* comprising administering an effective amount of a peptide represented by Formula (1) or Formula (2) to a patient:

$$R^1-NH-Cys-X^1 \quad (1)$$

(with cyclic structure containing S, C=O, $X^2$, $X^3$, $X^4$)

in Formula (1), $R^1$ is selected from the group consisting of a hydrogen atom, an amino acid and a derivative thereof, and, with or without substituent(s), an acyl group having 1 to 10 carbon atoms, a benzyloxycarbonyl group, a 9-fluorenylmethyloxycarbonyl group and a phenylisothiocyanate group, $X^1$ and $X^2$ are each independently selected from the group consisting of Ala, Gly, Trp, Met, Pro, Phe, Val, Leu, Ile, and Tyr, $X^3$ is any amino acid, and $X^4$ is selected from the group consisting of His, Ala, Thr, and Ser, with the proviso that, when $X^2$ is Phe, $X^4$ is Thr, when $X^4$ is Ala, $X^1$ is Ala, and when $X^4$ is Thr, $X^3$ is Trp or Ala;

$$R^2-N(Z-X^5)\cdots \quad (2)$$

(with cyclic structure containing $X^6$, $X^7$, $X^8$, C=O)

in Formula (2), $R^2$ is selected from the group consisting of a hydrogen atom, an amino acid and a derivative thereof, and, with or without substituent(s), an acyl group having 1 to 10 carbon atoms, a benzyloxycarbonyl group, a 9-fluorenylmethyloxycarbonyl group and a phenylisothiocyanate group, $X^5$ and $X^6$ are each independently selected from the group consisting of Ala, Gly, Trp, Met, Pro, Phe, Val, Leu, Ile, and Tyr, $X^7$ and $X^8$ are any amino acid, and Z is Cys, with the proviso that, when $X^6$ is Phe, $X^8$ is Thr, when $X^8$ is Ala, $X^5$ is Ala, and when $X^8$ is Thr, $X^7$ is Trp or Ala, wherein $X^6$ is selected from the group consisting of Phe, Trp, and Tyr, and/or $X^8$ is selected from the group consisting of His, Ala, Thr, and Ser.

11. The method according to claim 10, wherein the bacterium belonging to the genus *Clostridium* is *Clostridium welchii* (*Clostridium perfringens*).

12. A method for treating infections caused by a bacterium belonging to genus *Clostridium* comprising administering an effective amount of a cultured broth of *Clostridium butyricum* or a dried product of the broth to a patient, wherein the bacterium belonging to the genus *Clostridium* is *Clostridium welchii* (*Clostridium perfringens*).

13. The method according to claim 12, wherein *Clostridium butyricum* is *Clostridium butyricum* miyairi 588 (*Clostridium butyricum* MIYAIRI 588, FERM BP-2789).

14. The peptide according to claim 1, wherein (1-1) are represented by any one of (1-5) to (1-8):
(1-5) $X^1$ is Phe, $X^2$ is Trp, $X^3$ is Ala, and $X^4$ is His;
(1-6) $X^1$ is Leu, $X^2$ is Trp, $X^3$ is Ala, and $X^4$ is Thr;
(1-7) $X^1$ is Ala, $X^2$ is Trp, $X^3$ is Ala, and $X^4$ is Ala; and
(1-8) $X^1$ is Leu, $X^2$ is Trp, $X^3$ is Ala, and $X^4$ is Ser.

15. The peptide according to claim 3, wherein $X^1$, $X^2$, $X^3$ and $X^4$ in (2-1) are represented by any one of (2-5) to (2-8):
(2-5) $X^5$ is Phe, $X^6$ is Trp, $X^7$ is Ala, and $X^8$ is His;
(2-6) $X^5$ is Leu, $X^6$ is Trp, $X^7$ is Ala, and $X^8$ is Thr;
(2-7) $X^5$ is Ala, $X^6$ is Trp, $X^7$ is Ala, and $X^8$ is Ala; and
(2-8) $X^5$ is Leu, $X^6$ is Trp, $X^7$ is Ala, and $X^8$ is Ser.

* * * * *

SEQUENCE LISTING

```
<160> NUMBER OF SEQ ID NOS: 42

<210> SEQ ID NO 1
<211> LENGTH: 5
<212> TYPE: PRT
<213> ORGANISM: Artificial Sequence
<220> FEATURE:
<223> OTHER INFORMATION: THIOLEST

<400> SEQUENCE: 1

Cys Phe Trp Ala His
1               5

<210> SEQ ID NO 2
<211> LENGTH: 46
<212> TYPE: PRT
<213> ORGANISM: Staphylococcus aureus

<400> SEQUENCE: 2

Met Asn Thr Leu Phe Asn Leu Phe Phe Asp Phe Ile Thr Gly Ile Leu
1               5                   10                  15

Lys Asn Ile Gly Asn Ile Ala Ala Tyr Ser Thr Cys Asp Phe Ile Met
            20                  25                  30

Asp Glu Val Glu Val Pro Lys Glu Leu Thr Gln Leu His Glu
        35                  40                  45

<210> SEQ ID NO 3
<211> LENGTH: 44
<212> TYPE: PRT
<213> ORGANISM: Clostridium perfringens

<400> SEQUENCE: 3

Met Lys Lys Leu Asn Lys Asn Leu Leu Thr Leu Phe Ala Ala Leu Thr
1               5                   10                  15

Thr Val Val Ala Thr Thr Val Ala Thr Ser Ala Cys Leu Trp Phe Thr
            20                  25                  30

His Gln Pro Glu Glu Pro Lys Ser Leu Arg Asp Glu
        35                  40

<210> SEQ ID NO 4
<211> LENGTH: 41
<212> TYPE: PRT
```

<213> ORGANISM: Clostridium butyricum

<400> SEQUENCE: 4

Met Lys Thr Lys Ile Leu Met Gly Ile Ala Thr Val Ala Thr Val Met
1               5                   10                  15

Ala Ser Ile Val Ser Thr Ser Ala Cys Phe Trp Ala His Tyr Gln Pro
            20                  25                  30

Glu Glu Pro Lys Ser Leu Arg Glu Glu
        35                  40

<210> SEQ ID NO 5
<211> LENGTH: 6
<212> TYPE: PRT
<213> ORGANISM: Artificial Sequence
<220> FEATURE:
<223> OTHER INFORMATION: Cyclic peptide consisting of 6 amino acid
      residues

<400> SEQUENCE: 5

Ala Cys Phe Trp Ala His
1               5

<210> SEQ ID NO 6
<211> LENGTH: 7
<212> TYPE: PRT
<213> ORGANISM: Artificial Sequence
<220> FEATURE:
<223> OTHER INFORMATION: Cyclic peptide consisting of 7 amino acid
      residues

<400> SEQUENCE: 6

Ser Ala Cys Phe Trp Ala His
1               5

<210> SEQ ID NO 7
<211> LENGTH: 8
<212> TYPE: PRT
<213> ORGANISM: Artificial Sequence
<220> FEATURE:
<223> OTHER INFORMATION: Cyclic peptide consisting of 8 amino acid
      residues

<400> SEQUENCE: 7

Thr Ser Ala Cys Phe Trp Ala His
1               5

<210> SEQ ID NO 8
<211> LENGTH: 28
<212> TYPE: DNA
<213> ORGANISM: Artificial Sequence
<220> FEATURE:
<223> OTHER INFORMATION: PCR primer Sequence for amplification of DNA
      fragment including Clostridium butylicum agrD

<400> SEQUENCE: 8
ttggatcctc attggtacac agaaaaac                                      28

<210> SEQ ID NO 9
<211> LENGTH: 28
<212> TYPE: DNA
<213> ORGANISM: Artificial Sequence
<220> FEATURE:
<223> OTHER INFORMATION: PCR primer Sequence for amplification of DNA
      fragment including Clostridium butylicum agrD

<400> SEQUENCE: 9
aaaagcttat gggatgctgg tatctgag                                                28

<210> SEQ ID NO 10
<211> LENGTH: 20
<212> TYPE: DNA
<213> ORGANISM: Artificial Sequence
<220> FEATURE:
<223> OTHER INFORMATION: PCR primer Sequence for amplification of DNA
      fragment including Clostridium perfringens pfoA

<400> SEQUENCE: 10
gcaagtattg caatggcttt                                                         20

<210> SEQ ID NO 11
<211> LENGTH: 20
<212> TYPE: DNA
<213> ORGANISM: Artificial Sequence
<220> FEATURE:
<223> OTHER INFORMATION: PCR primer Sequence for amplification of DNA
      fragment including Clostridium perfringens pfoA

<400> SEQUENCE: 11
cttcatttcc ttctttgtca                                                         20

<210> SEQ ID NO 12
<211> LENGTH: 20
<212> TYPE: DNA
<213> ORGANISM: Artificial Sequence
<220> FEATURE:
<223> OTHER INFORMATION: PCR primer Sequence for amplification of DNA
      fragment including Clostridium perfringens plc

<400> SEQUENCE: 12
tttcctgggt tgtccatttc                                                         20

<210> SEQ ID NO 13
<211> LENGTH: 20
<212> TYPE: DNA
<213> ORGANISM: Artificial Sequence
<220> FEATURE:
<223> OTHER INFORMATION: PCR primer Sequence for amplification of DNA
      fragment including Clostridium perfringens plc

<400> SEQUENCE: 13
agtctacgct tgggatggaa                                                         20

<210> SEQ ID NO 14
<211> LENGTH: 30
<212> TYPE: DNA
<213> ORGANISM: Artificial Sequence
<220> FEATURE:
<223> OTHER INFORMATION: PCR primer Sequence for amplification of DNA
      fragment including Clostridium perfringens colA

<400> SEQUENCE: 14
ggatatgatg ctaaaaacac tgagttctat                                              30

<210> SEQ ID NO 15
<211> LENGTH: 22
<212> TYPE: DNA
<213> ORGANISM: Artificial Sequence
<220> FEATURE:
<223> OTHER INFORMATION: PCR primer Sequence for amplification of DNA
      fragment including Clostridium perfringens colA

<400> SEQUENCE: 15
cctgatgaat ttttccacca aa                                                      22

```
<210> SEQ ID NO 16
<211> LENGTH: 20
<212> TYPE: DNA
<213> ORGANISM: Artificial Sequence
<220> FEATURE:
<223> OTHER INFORMATION: PCR primer Sequence for amplification of DNA
      fragment including Clostridium perfringens VR-RNA

<400> SEQUENCE: 16
tgaaacatac aaaaaggatt                                                   20

<210> SEQ ID NO 17
<211> LENGTH: 20
<212> TYPE: DNA
<213> ORGANISM: Artificial Sequence
<220> FEATURE:
<223> OTHER INFORMATION: PCR primer Sequence for amplification of DNA
      fragment including Clostridium perfringens VR-RNA

<400> SEQUENCE: 17
tacaattatg gaatatgcaa                                                   20

<210> SEQ ID NO 18
<211> LENGTH: 20
<212> TYPE: DNA
<213> ORGANISM: Artificial Sequence
<220> FEATURE:
<223> OTHER INFORMATION: PCR primer Sequence for amplification of DNA
      fragment including Clostridium perfringens CPE0845

<400> SEQUENCE: 18
ccaatgtggt attgcttgtt                                                   20

<210> SEQ ID NO 19
<211> LENGTH: 20
<212> TYPE: DNA
<213> ORGANISM: Artificial Sequence
<220> FEATURE:
<223> OTHER INFORMATION: PCR primer Sequence for amplification of DNA
      fragment including Clostridium perfringens CPE0845

<400> SEQUENCE: 19
tgggaaaagt gaatttccag                                                   20

<210> SEQ ID NO 20
<211> LENGTH: 5
<212> TYPE: PRT
<213> ORGANISM: Artificial Sequence
<220> FEATURE:
<223> OTHER INFORMATION: THIOLEST

<400> SEQUENCE: 20

Cys Ala Trp Phe Ala
1               5

<210> SEQ ID NO 21
<211> LENGTH: 5
<212> TYPE: PRT
<213> ORGANISM: Artificial Sequence
<220> FEATURE:
<223> OTHER INFORMATION: THIOLEST

<400> SEQUENCE: 21

Cys Leu Trp Phe Ser
1               5
```

```
<210> SEQ ID NO 22
<211> LENGTH: 5
<212> TYPE: PRT
<213> ORGANISM: Artificial Sequence
<220> FEATURE:
<223> OTHER INFORMATION: THIOLEST

<400> SEQUENCE: 22

Cys Leu Phe Trp Thr
1               5

<210> SEQ ID NO 23
<211> LENGTH: 5
<212> TYPE: PRT
<213> ORGANISM: Artificial Sequence
<220> FEATURE:
<223> OTHER INFORMATION: SITE

<400> SEQUENCE: 23

Cys Phe Trp Ala His
1               5

<210> SEQ ID NO 24
<211> LENGTH: 5
<212> TYPE: PRT
<213> ORGANISM: Artificial Sequence
<220> FEATURE:
<223> OTHER INFORMATION: SITE

<400> SEQUENCE: 24

Cys Ala Trp Phe Ala
1               5

<210> SEQ ID NO 25
<211> LENGTH: 5
<212> TYPE: PRT
<213> ORGANISM: Artificial Sequence
<220> FEATURE:
<223> OTHER INFORMATION: SITE

<400> SEQUENCE: 25

Cys Leu Trp Phe Ser
1               5

<210> SEQ ID NO 26
<211> LENGTH: 5
<212> TYPE: PRT
<213> ORGANISM: Artificial Sequence
<220> FEATURE:
<223> OTHER INFORMATION: SITE

<400> SEQUENCE: 26

Cys Leu Phe Trp Thr
1               5

<210> SEQ ID NO 27
<211> LENGTH: 20
<212> TYPE: DNA
<213> ORGANISM: Artificial Sequence
<220> FEATURE:
<223> OTHER INFORMATION: Primer Sequence for Quantitative PCR of
      Clostridium perfringens pfoA

<400> SEQUENCE: 27
tgaagcacct ccacttatgg                                              20
```

<210> SEQ ID NO 28
<211> LENGTH: 22
<212> TYPE: DNA
<213> ORGANISM: Artificial Sequence
<220> FEATURE:
<223> OTHER INFORMATION: Primer Sequence for Quantitative PCR of
      Clostridium perfringens pfoA

<400> SEQUENCE: 28
gcatctcctc ctaaaactac tg

```
<211> LENGTH: 5
<212> TYPE: PRT
<213> ORGANISM: Artificial Sequence
<220> FEATURE:
<223> OTHER INFORMATION: SITE

<400> SEQUENCE: 34

Cys Ala Trp Ala Ala
1               5

<210> SEQ ID NO 35
<211> LENGTH: 5
<212> TYPE: PRT
<213> ORGANISM: Artificial Sequence
<220> FEATURE:
<223> OTHER INFORMATION: THIOLEST

<400> SEQUENCE: 35

Cys Leu Trp Ala Ser
1               5

<210> SEQ ID NO 36
<211> LENGTH: 5
<212> TYPE: PRT
<213> ORGANISM: Artificial Sequence
<220> FEATURE:
<223> OTHER INFORMATION: SITE

<400> SEQUENCE: 36

Cys Leu Trp Ala Ser
1               5

<210> SEQ ID NO 37
<211> LENGTH: 5
<212> TYPE: PRT
<213> ORGANISM: Artificial Sequence
<220> FEATURE:
<223> OTHER INFORMATION: THIOLEST

<400> SEQUENCE: 37

Cys Ala Trp Phe Thr
1               5

<210> SEQ ID NO 38
<211> LENGTH: 5
<212> TYPE: PRT
<213> ORGANISM: Artificial Sequence
<220> FEATURE:
<223> OTHER INFORMATION: THIOLEST

<400> SEQUENCE: 38

Cys Leu Trp Phe Ala
1               5

<210> SEQ ID NO 39
<211> LENGTH: 5
<212> TYPE: PRT
<213> ORGANISM: Artificial Sequence
<220> FEATURE:
<223> OTHER INFORMATION: THIOLEST

<400> SEQUENCE: 39

Cys Leu Ala Phe Thr
1               5

<210> SEQ ID NO 40
<211> LENGTH: 5
```

```
<212> TYPE: PRT
<213> ORGANISM: Artificial Sequence
<220> FEATURE:
<223> OTHER INFORMATION: THIOLEST

<400> SEQUENCE: 40

Cys Leu Trp Phe Thr
1               5

<210> SEQ ID NO 41
<211> LENGTH: 5
<212> TYPE: PRT
<213> ORGANISM: Artificial Sequence
<220> FEATURE:
<223> OTHER INFORMATION: THIOLEST

<400> SEQUENCE: 41

Cys Leu Trp Tyr Thr
1               5

<210> SEQ ID NO 42
<211> LENGTH: 5
<212> TYPE: PRT
<213> ORGANISM: Artificial Sequence
<220> FEATURE:
<223> OTHER INFORMATION: THIOLEST

<400> SEQUENCE: 42

Cys Leu Phe Trp Ser
1               5
```